US012203929B2

(12) United States Patent
Kauffman et al.

(10) Patent No.: US 12,203,929 B2
(45) Date of Patent: Jan. 21, 2025

(54) HYBRID QUANTUM-CLASSICAL COMPUTING SYSTEM AND METHOD

(71) Applicants: The University of Vermont, Burlington, VT (US); Tampere University of Technology, Tampere (FI)

(72) Inventors: Stuart Kauffman, Santa Fe, NM (US); Samuli Niiranen, Tampere (FI); Gábor Vattay, Budapest (HU)

(73) Assignees: The University of Vermont, Burlington, VT (US); Tampere University of Technology, Tampere (FI)

( * ) Notice: Subject to any disclaimer, the term of this patent is extended or adjusted under 35 U.S.C. 154(b) by 1477 days.

(21) Appl. No.: 16/446,354

(22) Filed: Jun. 19, 2019

(65) Prior Publication Data
US 2019/0302107 A1    Oct. 3, 2019

Related U.S. Application Data

(60) Continuation-in-part of application No. 15/957,883, filed on Apr. 19, 2018, now abandoned, which is a
(Continued)

(51) Int. Cl.
| | |
|---|---|
| *G01N 33/48* | (2006.01) |
| *B82Y 10/00* | (2011.01) |
| *G01N 33/50* | (2006.01) |
| *G01N 33/543* | (2006.01) |
| *G06N 10/00* | (2022.01) |
| *G16B 35/00* | (2019.01) |

(Continued)

(52) U.S. Cl.
CPC ........ *G01N 33/54366* (2013.01); *B82Y 10/00* (2013.01); *G06N 10/00* (2019.01); *G16B 35/00* (2019.02); *G16C 20/50* (2019.02); *G16C 20/60* (2019.02); *G01N 2500/04* (2013.01); *G01N 2500/20* (2013.01)

(58) Field of Classification Search
CPC ......... G01N 33/54366; G01N 2500/04; G01N 2500/20; B82Y 10/00; G06N 10/00; G16B 35/00; G16C 20/50; G16C 20/60
See application file for complete search history.

(56) References Cited

U.S. PATENT DOCUMENTS

| 7,904,283 B2 | 3/2011 | Merz, Jr. et al. |
| 8,849,580 B2 | 9/2014 | Kauffman et al. |
| | (Continued) | |

OTHER PUBLICATIONS

Aleksandrowicz et al.: "Classical simulators for quantum computers," Medium, downloaded Dec. 18, 2019 from https://medium.com/giskit/classical-simulators-for-quantum-computers-4b994dad4fa2; 6 pages.

(Continued)

*Primary Examiner* — Russell S Negin
(74) *Attorney, Agent, or Firm* — Knobbe, Martens, Olson & Bear LLP

(57) ABSTRACT

Disclosed herein are systems and uses of systems operating between fully quantum coherent and fully classical states. Examples include a hybrid quantum-classical computing system comprising a plurality of quantum processors connected via classical means.

14 Claims, 8 Drawing Sheets

Related U.S. Application Data continuation of application No. 14/500,901, filed on Sep. 29, 2014, now abandoned, which is a division of application No. 13/187,257, filed on Jul. 20, 2011, now Pat. No. 8,849,580.

(60) Provisional application No. 61/431,420, filed on Jan. 10, 2011, provisional application No. 61/420,720, filed on Dec. 7, 2010, provisional application No. 61/416,723, filed on Nov. 23, 2010, provisional application No. 61/367,781, filed on Jul. 26, 2010, provisional application No. 61/367,779, filed on Jul. 26, 2010.

(51) Int. Cl.
G16C 20/50 (2019.01)
G16C 20/60 (2019.01)

(56) References Cited

U.S. PATENT DOCUMENTS

| | | | |
|---|---|---|---|
| 9,152,746 B2 | 10/2015 | Troyer et al. | |
| 2007/0174227 A1* | 7/2007 | Johnson | B82Y 10/00 706/62 |
| 2008/0313430 A1* | 12/2008 | Bunyk | G06N 10/00 712/E9.082 |
| 2009/0319757 A1* | 12/2009 | Berkley | G06N 10/00 257/31 |
| 2015/0024964 A1 | 1/2015 | Kauffman et al. | |

OTHER PUBLICATIONS

Ashkenasy et al., Boolean Logic Functions of a Synthetic Peptide Network, JACS Aug. 19, 2004, 126(36): 11140-11141.
Ashkenasy et al., Design of a directed molecular network, PNAS, Jul. 27, 2004, 101(30): 10872-10877.
Bachmann et al., Autocatalytic self-replicating micelles as models for prebiotic structures, Nature, May 7, 1992, 357: 57-59.
Bachmann et al., Self-Replicating Reverse Micelles and Chemical Autopoiesis, J Am Chem Soc. 1990, 112: 8200-8201.
Berkley et al. A scalable readout system for a superconducting adiabatic quantum optimization system, Mar. 24, 2010.
Bieberich, Erhard, Non-local Quantum evolution of entangled ensemble states in neural nets and its significance for brain function and a theory of consciousness; revised Version Jul. 26, 1999; retrieved Oct. 11, 2013 from http://arxiv.org/html/quant-ph/9906011v2; 15 pages.
Bliokh et al., Tunable electronic transport and unidirectional quantum wires in graphene subjected to electric and magnetic fields; Phys Review 2010; B81: 075410-1-075410-9.
Caivano et al., Feshbach resonance and mesoscopic phase separation near a quantum critical point in multiband FeAs-based superconductors, Supercond Sci Technol., 2008, preprint from arXiv0809.4865; 31 pages.
Cao et al., Optimization of Exciton Trapping in Energy Transfer Processes, J Phys Chem A, Dec. 17, 2009, 113(50): 13825-13838.
Cartlidge, Edwin, Physicists create a living laser; physicsworld.com Jun. 12, 2011, retrieved Oct. 11, 2013 from http://physicsworld.com/cws/article/news/2011/jun/12/physicists-create-a-living-laser; 2 pages.
Chan, Sunney I., Exciton Interation. Hypo- and Hyper-chromism; Biophyscial Chemistry 24a, Winter Term 2009/2010, Feb. 1, 2010; PowerPointPresentation, 10 pages.
Collini et al., Coherent Intrachain Energy Migration in a Conjugated Polymer at Room Temperature, Science 2009, 323: 369-373.
Collini et al., Coherently wired light-harvesting in photosynthetic marine algae at ambient temperature, Nature Feb. 4, 2010, 463: 644-647.
Cormick et al., Observing different phases for the dynamics of entanglement in an ion trap, Phys Rev A, 2010, 81: 022306-1 to 022306-5.
Day, Charles, Month-long calculation resolves 82-year-old quantum paradox; Search & Discovery, Physics Today Sep. 2009, pp. 16-17.
de la Lande et al., Transmission Coefficients for Chemical Reactions with Multiple States: Role of Quantum Decoherence; JACS 2011, 133: 3883-3894.
de Oliviera et al., Probing of the quantum dot size distribution in CdTedoped glasses by photoluminexcence excitation spectroscopy, Appl Phys Lett. 1995, 66: 439-.
Diaz-Pier et al. Classical Simulation of Quantum Adiabatic Algorithms using Mathematica on GPUs, Mar. 5, 2011.
Dotta et al., Photon emissions from human brain and cell culture exposed to distally rotating magnetic fields shared by separate light-stimulated brains and cells; Brain Research, 2011, 1388: 77-88.
Driel et al., Frequency-Dependent Spontaneous Emission Rate from CdSe and CdTe nanocrystals: Influence of Dark States; Phys Review Ltts; 2005, 95: 236804-1 to 236804-4.
Fischer et al., Observation of the Quantum Zeno and Anti-Zeno Effects in an Unstable System, Phys Rev Lett. Jul. 23, 2001, 85(4): 040402-1 to 040402-4.
Franson et al., Generation of entangled ancilla states for use in linear optics quantum computing, Phys Rev A, 2004, 69: 052328-1 to 052328-7.
Fratini et al., Scale-free structural organization of oxygen interstitials in La2CuO4+y, Nature, Aug. 12, 2010, 466: 841-844.
Galve et al., Bringing Entanglement to the High Temperature Limit, Phys Rev Lett Oct. 29, 2010, 105: 180501-1 to 180501-4.
Gauger et al., Sustained Quantum Coherence and Entanglement in the Avian Compass, Phys Rev Lett. Jan. 28, 2011, 106: 040503-1 to 040503-.
Goto et al. Combinatorial optimization by simulating adiabatic bifurcations in nonlinear Hamiltonian systems, Sci. Adv. 2019, pp. 1-8.
Ihexis LLC, Programmable Matter Super-Turing Hypercomputers; Dec. 1, 2008, 13 pages.
Inagaki et al. A coherent Ising machine for 2000-node optimization problems, Science, vol. 354, Issue 6312, pp. 603-606, Nov. 4, 2016.
Itano et al., Quantum Zeno effect, Phys Review A, Mar. 1, 1990, 41(5): 2295-2300.
Kauffman, Stuart, Agents, Or How Doing Leads To Values, Blog posted May 10, 2010; retrieved Oct. 10, 2013 from http://www.npr.org/blogs/13.7/2010/05/10/126714358/agency-doing-values-and-ought; 4 pages.
Kauffman, Stuart, Beyond Einstein and Schrodinger? The Quantum Mechanics of Closed Quantum Systems; Blog posted Nov. 22, 2010; retrieved Oct. 10, 2013 from http://www.npr.org/blogs/13.7/2010/11/22/131510041/beyond-einstein-and-schrodinger-the-quantum-mechanics-of-closed-quantum-systems; 4 pages.
Kauffman, Stuart, Can A Changing Adjacent Possible Acausally Change History? The Open Universe IV, Bog posted Feb. 25, 2010; retrieved Oct. 10, 2013 from http://www.npr.org/blogs/13.7/ 2010/02/can_a_changing_adjacent_possib.html; 9 pages.
Kauffman, Stuart, Can We Have A Responsible Free Will? Blog posted Jan. 31, 2011; retrieved Oct. 10, 2013 from http://www.npr.org/blogs/13.7/2011/01/31/133319117/can-we-have-a-responsible-free-will; 3 pages.
Kauffman, Stuart, Complexity Theory: Normal Science and Frontiers Classical and Quantum, Private Paper Nov. 6, 2010; 49 pages.
Kauffman, Stuart, Contemporary Work On The Origin of Life, Blog posted May 17, 2010; retrieved Oct. 10, 2013 from http://www.npr.org/blogs/13.7/2010/05/05/126532686/contemporary-work-on-the-origin-of-life; 6 pages.
Kauffman, Stuart, Free Will: There Are No Easy Answers; Blog posted Aug. 23, 2010; retrieved Oct. 10, 2013 from http://www.npr.org/blogs/13.7/2011/02/18/129375622/free-will; 6 pages.
Kauffman, Stuart, How Can Mind Act On Matter? Blog posted Mar. 22, 2010; retrieved Oct. 10, 2013 from http://www.npr.org/blogs/13.7/2010/03/how_can_mind_act_on_matter.html; 9 pages.

(56) References Cited

OTHER PUBLICATIONS

Kauffman, Stuart, How Mind Can Act Acausally On Brain? Blog posted Dec. 27, 2010; retrieved Oct. 10, 2013 from http://www.npr.org/blogs/13.7/2010/12/27/132361145/how-mind-can-act-acausally-on-brain; 4 pages.

Kauffman, Stuart, Is The Human Mind Algorithmic? Blog posted Mar. 15, 2010; retrieved Oct. 10, 2013 from http://www.npr.org/blogs/13.7/2010/03/is_the_human_mind_algorithmic_1.html; 6 pages.

Kauffman, Stuart, Is There a 'Poised Realm' Between the Quantum and Classical Worlds? Blog posted Mar. 3, 2010; retrieved Oct. 10, 2013 from http://www.npr.org/blogs/13.7/2010/03/is_there_a_poised_realm_betwee.html; 7 pages.

Kauffman, Stuart, Res Extensa, Res Potentia And The Poised Realm; Blog posted Aug. 17, 2010; retrieved Oct. 10, 2013 from http://www.npr.org/blogs/13.7/2010/08/17/129250892/res-extensa-res-potentia-and-the-poised-realm; 7 pages.

Kauffman, Stuart, Standing The Brain On Its Head; Blog posted Jan. 30, 2011; retrieved Oct. 10, 2013 from http://www.npr.org/blogs/13.7/2011/01/30/133319070/standing-the-brain-on-its-head; 5 pages.

Kauffman, Stuart, The Hard Problem: Consciousness; Blog posted Mar. 30, 2010; retrieved Oct. 10, 2013 from http://www.npr.org/blogs/13.7/2010/03/the_hard_problem_conscousness.html; 8 pages.

Kauffman, Stuart, The Non-Algorithmic Trans-Turing System; Blog posted Dec. 14, 2010; retrieved Oct. 10, 2013 from http://www.npr.org/blogs/13.7/2010/12/14/132039092/the-non-algorithmic-trans-turing-system; 4 pages.

Kauffman, Stuart, The 'Poised Realm' Is Real; Blog posted Dec. 6, 2010; retrieved Oct. 10, 2013 from http://www.npr.org/blogs/13.7/2010/12/06/131846605/the-poised-ream-is-real; 4 pages.

Kauffman, Stuart, The Quantum Mechanics Of Open Quantum Systems; Blog posted Nov. 29, 2010; retrieved Oct. 10, 2013 from http://www.npr.org/blogs/13.7/2010/11/24/131567335/the-quantum-mechanics-of-open-quantum-systems; 4 pages.

Kauffman, Stuart, To Be Is To Be Perceived: A Clue To The Observer Quantum Measurement Problem; Blog posted Apr. 7, 2010; retrieved Oct. 10, 2013 from http://www.npr.org/blogs/13.7/2010/04/to_be_is_to_be_perceived_the_q.html; 6 pages.

Kauffman, Stuart, Toward A Responsible Free Will; Blog posted Mar. 26, 2010; retrieved Oct. 10, 2013 from http://www.npr.org/blogs/13.7/2010/03/towards_a_responsible_free_wil_1.html; 7 pages.

Kauffman, Stuart, We Seem To Be Zombies; Blog posted Dec. 20, 2010; retrieved Oct. 10, 2013 from http://www.npr.org/blogs/13.7/2010/12/20/132203880/we-seem-to-be-zombies; 5 pages.

Kauffman, Stuart, What Is Consciousness? A Hypothesis; Blog posted Jan. 19, 2011; retrieved Oct. 10, 2013 from http://www.npr.org/blogs/13.7/2011/01/29/133318986/what-is-consciousness-a-hypothesis; 2 pages.

Kaulakys et al., Quantum anti-Zeno effect, Phys Rev A, Aug. 1997, 56(2): 1131-1137.

Kocherzhenko et al., Charge Transfer Through Molecules with Multiple Pathways: Quantum Interference and Dephasing, J Phys Chem C. 2010, 114(17): 7973-7979.

Kokail et al. Self-verifying variational quantum simulation of lattice models, Nature, vol. 569, pp. 355-360.

Kotter et al., Solar Nantenna Electromagnetic Collectors; 2nd International Conference on Energy Sustainability Aug. 2008; Idaho National Laboratory ES 2008-54016; 8 pages.

Kottos et al., Periodic Orbit Theory and Spectral Statistics for Quantum Graphs, Annals Phys. 1999, 274: 76-124.

Kurzweil Accelerating Intelligence, Researchers use high magnetic fields to suppress decoherence, paving the way for quantum computing; Jul. 21, 2011, retrieved Oct. 11, 2013 from http://physicsworld.com/cws/article/news/2011/jun/12/physicists-create-a-living-laser; 1 page.

Lincoln et al., Self-Sustained Replication of an RNA Enzyme, Science, Feb. 27, 2009, 323: 1229-1232.

Luisi et al., A Possible Route to Prebiotic Vesicle Reproduction, MIT; Artificial Life 2004, 10: 297-308.

Luisi et al., Self-Replicating Micelles—A Chemical Version of a Minimal Autopoietic System, Origins of Life and Evolution of the Biosphere, 1989, 19: 633-643.

Lukk et al., A global map of human gene expression, Correspondence to Editor; Nature Biotech. Apr. 2010, 28(4): 322-324.

Mcmahon et al. A fully-programmable 100-spin coherent lsing machine with all-to-all connections, Science, pp. 1-8, Oct. 20, 2016.

Nayakar et al., Quantum randomness and free will, Poornaprajna Institute of Scientific Research, Sadashivnagar, Bangalore; Nov. 22, 2010, 11 pages.

Nazarkin et al., Electromagnetically Induced Quantum Memory, Phys Rev Lett. Jan. 30, 2004, 92(4): 043002-1 to 043002-4.

Palla et al., Spectral transitions in networks, New J Phys. Dec. 6, 2006, 8: 307-317.

Pattanayak et al., Exponentially Rapid Decoherence of Quantum Chaotic Systems, Phys Rev Lett. Nov. 24, 1997, 79(21): 4131-4134.

Pattanayak, Arjendu K., Lyapunov Exponents, Entropy Producation, and Decoherence, Phys Rev Lett. Nov. 29, 1999, 83(22): 4526-4529.

Paz et al., Dynamics of the Entanglement between Two Oscaillators in the Same Environment, Phys Rev Lett. Jun. 6, 2008, 100: 220401-1 to 220401-4.

Paz et al., Entanglement dynamics during decoherence, Quantum Inf Process-Springer Science+Business Media, 2009, 8: 535-548.

Paz et al., Redundancy of classical and quantum correlations during decoherence, Phys Rev A, 2009, 80: 042111-1 to 042111-6.

PCE Stamp, Decoherence: Fact & Fiction, presented at Orcas Island on Jul. 19, 2010 by faculty of UBC Vancouver, Physics & Astronomy Department et al., PowerPoint Presentation, 46 pages.

Pessa, Eliano, Phase Transitions in Biological Matter, Università di Pavia, Udine, Italy, Research Paper Sep. 2007, 64 pages.

Prezhdo, Oleg V., Quantum Anti-Zeno Acceleration of a Chemical Reaction, Phys Rev Lett. Nov. 20, 2000, 85(21): 4413-4417.

Reich, Eugenie Samuel, Quantum theorem shakes foundations—The wavefunction is a real physical object after all, say researchers; Nature/News Nov. 17, 2011; retrieved Oct. 11, 2013 from http://www.nature.com/news/quantum-theorem-shakes-foundations-1.9392; 3 pages.

Rigaud et al., Reconstitution of membrane proteins into liposomes: application to energy transducing membrane proteins; Biochim Biophys Acta, 1995, 1231: 223-246.

Ruyant, Quentin, Quantum Physics and the Ontology of Mind—Focus Issue, J Conscious Expl Res. Nov. 2010, 1(8): 1027-1047.

Sanders, Laura, Everyday entanglement: Physicists take quantum weirdness out of the lab; Science News, Nov. 20, 2010, 178(11): 22-29.

Sanderson, Katharine, A demon of a device—Light makes molecular machines perform trick; Nature/News Jan. 31, 2007; retrieved Oct. 11, 2013 from http://www.nature.com/news/2007/070129/full/news070129-10.html; 2 pages.

Sargent, Edward H., Infrared Optoelectronics You Can Apply With a Brush; IEEE Spectrum Feb. 2010; 5 pages.

Sargent, Edward H., Infrared photovoltaics made by solution processing, Nature Photonics May 28, 2009; 3: 325-331.

Scholes, Gregory D., Quantum-Coherent Electronic Energy Transfer: Did Nature Think of It First? J Phys Chem Lett. Jan. 7, 2010, 1: 2-8.

Scholes, Gregory D., Quantum-Mechanical Optimization of Light-Harvesting in Photosynthesis, Lecture Outline, Fall 2010 University of Vermont, Theoretical and Applied Physics; 1 page [Abstract Only].

Susumu et al., Conjugated Chromophore Arrays with Unusually Large Hole Polaron Delocalization Lengths; JACS Jun. 9, 2006, 128: 8380-8381.

Tiwari et al., Electronic resonance with anticorrelated pigment vibrations drives photosynthetic energy transfer outside the adiabatic framework, PNAS Jan. 22, 2013, 110(4): 1203-1208.

Vattay et al., Quantum biology on the edge of quantum chaos; Feb. 29, 2012; arXiv: 1202.6433v1; 5 pages.

Viola et al., Dynamical suppression of decoherence in two-state quantum systems, Phys Review Oct. 1998, 58(4): 2733-2744.

(56) References Cited

OTHER PUBLICATIONS

Wagner et al., Systems Chemistry: Logic Gates, Arithmetic Units, and Network Motifs in Small Networks, Chem Eur J. 2009 (online: Dec. 23, 2008), 15: 1765-1775.
Wang et al., Vibrationally coherent photochemistry in the femtosecond primary event of vision, Science, New Series, Oct. 21, 1994, 266(5184): 422-424.
Weinstein et al., The Edge of Quantum Chaos, MIT Paper #206039, Version 2, Oct. 3, 2002, 4 pages.
WEIZMANN Institute of Science, Biological molecules select their spin; Phys.org Mar. 31, 2011, retrieved Oct. 11, 2013 from http://phys.org/news/2011-03-biological-molecules.html; 1 page.
Wilkinson et al., Experimental evidence for non-exponential decay in quantum tunnelling, Nature Jun. 5, 1997, 387: 575-549.
Wolynes, Peter G., Some quantum weirdness in physiology, Commentary, PNAS Oct. 13, 2009, 106(41): 17247-17248.
Womick et al., Toward the origin of exciton electronic structure in phycobiliproteins, J Chem Phys. Jul. 14, 2010, 133: 024507-1 to 024507-10.
Zhu et al., Closed loop learning control to suppress the effects of quantum decoherence, J Chem Phys. Apr. 15, 2003, 118(15): 6751-6757.
Zhu et al., Pure phase decoherence in a ring geometry; Phys Review Jun. 25, 2010; A81: 16 pages.
Zyga, Lisa, Quantum explanation for how we smell gets new support; Phys.org Mar. 28, 2011, retrieved Oct. 11, 2013 from http://phys.org/news/2011-03-quantum-explanation.html; 2 pages.
Zyga, Lisa, Quantum mechanics may explain how humans smell; Phys.org Feb. 1, 2007, retrieved Oct. 11, 2013 from http://phys.org/news89542035.html; 2 pages.

\* cited by examiner

HYBRID QUANTUM-CLASSICAL COMPUTING SYSTEM AND METHOD

CROSS-REFERENCE TO RELATED APPLICATIONS

This application is a continuation-in-part of U.S. application Ser. No. 15/957,883, filed Apr. 19, 2018, which is a continuation of U.S. application Ser. No. 14/500,901, filed Sep. 29, 2014, which is a divisional of U.S. application Ser. No. 13/187,257, filed Jul. 20, 2011, now U.S. Pat. No. 8,849,580, which claims the benefit of U.S. Provisional Application No. 61/367,781, filed Jul. 26, 2010; 61/367,779, filed Jul. 26, 2010; 61/416,723, filed Nov. 23, 2010; 61/420,720, filed Dec. 7, 2010; and 61/431,420, filed Jan. 10, 2011, all of which are incorporated herein by reference in their entirety.

BACKGROUND

Field of the Invention

The present invention relates to the field of quantum computing.

Background Description

One of the greatest challenges of quantum computing is to maintain the quantum coherence and quantum entanglement of qubits. Coherence degrades exponentially with the number of qubits in a fully quantum computer processor and there is a theoretical limit on the exponent of the degradation [Unruh, 1995] setting a hard physical limit on the number of fully coherent qubits that can be integrated in a single processor.

Quantum computing has been realized on various physical devices. The most robust realizations use macroscopic quantum phenomena such as superconducting quantum devices [Johnson et al., 2011] and laser based optical qubits [Inagaki et al., 2016, McMahon et al., 2016]. In both cases qubit states are realized by a macroscopic number of electrons or photons, not by a fragile single quantum state.

There are two main quantum computing concepts as of today. Standard quantum computation [Nielsen and Chuang, 2010] is performed by quantum circuits, which are similar to classical circuits, except that quantum gates (such as Hadamard and controlled-NOT) are used instead of classical gates (such as OR and NOT). Adiabatic quantum computation [Farhi et al., 2000] is specified by two Hamiltonians named $H_{init}$ and $H_{final}$, where a Hamiltonian is simply a Hermitian matrix. The eigenvector with smallest eigenvalue (also known as the ground state) of $H_{init}$ is required to be an easy-to-prepare state, such as a tensor product state. The output of the adiabatic computation is the ground state of the final Hamiltonian $H_{final}$. The running time of the adiabatic computation is determined by the minimal spectral gap of the transitional Hamiltonian $$\hat{H}_{tr}(s) = (1-s)\hat{H}_{ini} + s\hat{H}_{fin}, \quad (1)$$

for $s \in [0, 1]$. In particular, the adiabatic computation runs in polynomial time if this minimal spectral gap is at least inverse polynomial. It has been shown [Aharonov et al., 2008] that the adiabatic computation model and the standard circuit-based quantum computation model are polynomially equivalent. The equivalence between the models allows one to state the main open problems in quantum computation using well-studied mathematical objects such as eigenvectors and spectral gaps of Hamiltonians.

Adiabatic quantum computing is based on solving the time dependent Schrödinger equation $$\hbar \partial_t \psi(t) = \hat{H}_{tr}(t/T_A)\psi(t) = [(1-t/T_A)\hat{H}_{ini} + (t/T_A)\hat{H}_{fin}]\psi(t) \quad (2)$$

where $T_A$ is the time of the adiabatic (slow) transition from the initial to the final Hamiltonian operator. The wave function initialized such a way that at the start of the process it is the ground state of the initial Hamilton operator $$E_0(0)\psi(0) = \hat{H}_{ini}\psi \quad (0).$$

Then the adiabatic theorem of quantum mechanics [Bransden and Joachain, 2000] assures that the final wave function $\psi(T_A)$ converges to the ground state of the final Hamiltonian $$E_0(T_A)\psi(T_A) = \hat{H}_{fin}\psi(T_A),$$

if the transition is sufficiently slow, i.e. $T_A \to \infty$. In particular, if the ground state $E_0$s) and the first excited state $E_1$(s) of the transitional Hamiltonian $\hat{H}_{tr}(s)$ has a minimum spectral gap $$g_{min} = \min_{s \in [0,1]} \{E_1(s) - E_0(s)\} \quad (3)$$

the annealing time should be $$T_A \gg \varepsilon_{min} \hbar / g_{min}^2$$

[Farhi it al., 2000], where $\varepsilon$ is the maximum of the expectation value $$\varepsilon = \max_{s \in [0,1]} \langle \psi_0(s) | \hat{H}_{fin} - \hat{H}_{ini} | \psi_0(s) \rangle.$$

In real world realizations of adiabatic quantum computation [Johnson et al., 2011] a convenient choice for the final Hamiltonian is the Ising Hamiltonian $$H_{fin} = \sum_i h_i \sigma_i^z + \sum_{ij} J_{ij} \sigma_i^z \sigma_j^z, \quad (4)$$

where $\sigma^z$ represent Pauli matrix operators acting on spin states, and $$H_{ini}(\sigma_1^x, \ldots, \sigma_N^x) = -\Delta \sum_i \sigma_i^x, \quad (5)$$

for the initial Hamiltonian, where $\sigma_i^x$ is the Pauli matrix operator representing a spin operator in the transverse direction. The Ising Hamiltonian is originated in solid state physics, where it describes pair interactions of magnetic moments. In computational problems interactions of more than two qubits can be allowed, which can be represented by the final Hamiltonian $$H_{fin}(\sigma_1^z, \ldots, \sigma_N^z) = \sum_i h_i \sigma_i^z + \sum_{i<j} J_{ij}^{(2)} \sigma_i^z \sigma_j^z + \sum_{i<j<k} J_{ijk}^{(3)} \sigma_i^z \sigma_j^z \sigma_k^z + \ldots \quad (6)$$

where H $(\sigma_1^z, \ldots, \sigma_N^z)$ can be an analytic function of its variables and $J_{ij}^{(2)}$, $J_{ijk}^{(3)}$, ... represent higher order expansion coefficients of the power series of the Hamiltonian. The final Hamiltonian is a many-body Hamiltonian where qubits can be regarded as one-body systems and their interactions are described by the non-linear terms with strengths $$J_{ij}^{(2)}, J_{ijk}^{(3)}, \ldots \; ij \; ijk$$

The variational principle is the basis of the variational method used in quantum mechanics and quantum chemistry to find approximations to the ground state. For a Hamiltonian $\hat{H}$ that describes the studied system and any realizable function $\Psi$ with arguments appropriate for the unknown wave function of the system, we define the functional $$\varepsilon[\Psi] = \frac{\langle \Psi | \hat{H} | \Psi \rangle}{\langle \Psi | \Psi \rangle}.$$

The variational principle states that $\varepsilon \geq E_0$, where $E_0$ is the lowest energy eigenstate (ground state) of the Hamiltonian $\varepsilon = E_0$ if and only if $\Psi$ is exactly equal to the wave function of the ground state of the studied system.

A variational method for finding approximate solutions of the time-dependent Schrödinger equation has also been developed [McLachlan, 1964]. For many-body interacting systems it leads to the time-dependent Hartree equations [Slater, 1930]. An approximate time-dependent wave function for N quantum mechanical systems which interact with one another. The systems are supposed to be distinguishable. The wave function is taken to be a product of normalized one-body wave functions $$\Psi(t) = \prod_{i=1}^{N} \psi_i(q_i, t), \tag{7}$$

at all times, where $q_i$ stands for the quantum variables (coordinates, spins, etc.) of system I and where the Hamiltonian is $$\hat{H} = \sum_i \hat{H}(q_i) + \sum_{i<j} \hat{V}_{ij}(q_i, q_j). \tag{8}$$

The Dirac-Frenkel-McLachlan (DFM) time-dependent self-consistent equations are $$i\hbar \partial_t \psi_i(q_i, t) = (\hat{H}_i + \hat{G}_i)\psi_i(q_i, t). \tag{9}$$

where $$\hat{G}_i(q_i) = \sum_{ij \neq i} \int \psi_j^*(q_j) \hat{V}_{ij}(q_i, q_j) \psi_j(g_j) dg_j. \tag{10}$$

SUMMARY OF THE INVENTION

Some embodiments described herein include a hybrid quantum-classical computer, comprising:

a first quantum processor comprising a first plurality of entangled qubits;
a second quantum processor comprising a second plurality of entangled qubits;
a first plurality of detectors coupled to the first quantum processor and configured to read a state of each of the first plurality of qubits;
a classical processor coupled to the first plurality of detectors and configured to determine a first plurality of outputs based on the states of the first plurality of qubits; and
a first plurality of signal generators coupled to the classical processor and the second quantum processor and configured to generate and apply a plurality of signals based on the first plurality of outputs to the second plurality of qubits.

In some embodiments, the qubits are superconducting qubits. In some embodiments, the state comprises a charge quanta. In some embodiments, the state comprises a magnetic flux quanta. In some embodiments, the qubits comprise an ac SQUID. In some embodiments, the first plurality of detectors comprise a dc SQUID for each of the first plurality of qubits. In some embodiments, the first plurality of detectors comprise a quantum flux parametron for each of the first plurality of qubits. In some embodiments, each quantum flux parametron is positioned adjacent to a qubit in the first plurality of qubits. In some embodiments, each dc SQUID is positioned adjacent to one of the quantum flux parametrons. In some embodiments, the first plurality of signal generators are configured to generate magnetic fields that are inductively coupled to the second plurality of qubits. In some embodiments, the first plurality of signal generators comprise a dc SQUID for each of the second plurality of qubits. In some embodiments, the first plurality of signal generators comprise a quantum flux parametron for each of the second plurality of qubits. In some embodiments, each quantum flux parametron is positioned adjacent to a qubit in the second plurality of qubits. In some embodiments, each dc SQUID is positioned adjacent to one of the quantum flux parametrons. In some embodiments, the state comprises a quantum charge oscillation. In some embodiments, the qubits are optical qubits. In some embodiments, the state comprises a degenerate optical parametric oscillator phase. In some embodiments, the first plurality of detectors comprise homodyne detectors. In some embodiments, the first and second quantum processors comprise a field-programmable gate array (FPGA) configured to generate a feedback signal. In some embodiments, the first plurality of signal generators include the FPGA and are configured to combine the feedback signal with the first plurality of signals determined from the state of each of the first plurality of qubits. In some embodiments, the classical processor is configured to determine the first plurality of outputs using a weighted linear combination of the states of the first plurality of qubits. In some embodiments, the weights are based on interaction values between the qubits in first plurality of qubits and the qubits in the second plurality of qubits in a final Hamiltonian whose eigenvalue solution is desired.

In some embodiments, the computer comprises:

a second plurality of detectors coupled to the second quantum processor and the classical processor and configured to read a state of each of the second plurality of qubits, wherein the classical processor is further configured to determine a second plurality of outputs based on the states of the second plurality of qubits; and
a second plurality of signal generators coupled to the classical processor and the first quantum processor and configured to generate and apply a second plurality of signals based on the second plurality of outputs to the first plurality of qubits.

In some embodiments, the first plurality of detectors are configured to also operate as the second plurality of signal generators and the first plurality of signal generators are configured to also operate as the second plurality of detectors.

In some embodiments, the computer comprises:
one or more additional quantum processors, each comprising a plurality of entangled qubits; and
one or more additional sets of signal generators coupled to the classical processor, wherein the one or more additional sets of signal generators are configured to generate and apply signals based on the first plurality of outputs to the qubits in the one or more additional quantum processors.

Other embodiments disclosed herein include a method of computation, comprising:
providing a first set of entangled qubits;
providing a second set of entangled qubits not entangled with the first set of qubits;
reading a state of each of the qubits in the first set; and
applying a signal to each of the qubits in the second set, wherein each signal is determined by a weighted combination of the states of the qubits in the first set.

In some embodiments, the first and second sets of qubits are superconducting qubits. In some embodiments, applying the signals to the qubits in the second set comprises using inductive coupling. In some embodiments, the qubits comprise ac SQUIDs and the signals are applied by inductively coupled dc SQUIDs. In some embodiments, the qubits comprise ac SQUIDs and the signals are applied by inductively coupled quantum flux parametrons and dc SQUIDs. In some embodiments, reading the state of the qubits in the first set comprises measuring currents in the qubits in the first set. In some embodiments, measuring the currents comprises using dc SQUIDs inductively coupled to the qubits. In some embodiments, reading a state of each of the qubits in the second set. In some embodiments, the first and second sets of qubits are optical qubits. In some embodiments, reading the states of the qubits in the first set comprises measuring degenerate optical parametric oscillator phase of the qubits in the first set. In some embodiments, the measurements are conducted using a beam splitter and homodyne detector. Some embodiments include applying the signals comprise combining the signals with a feedback signal used to generate the qubits. In some embodiments, the combined signals are applied using a field-programmable gate array. In some embodiments, reading the state of the qubits comprises measuring the mean values of the qubits. In some embodiments, reading the state of the qubits in the first set and applying the signals to the qubits in the second set comprises using high frequency electronics. In some embodiments, the signals are determined using a classical processor that receives the read state of the qubits in the first set. Some embodiments include providing a plurality of additional sets of entangled qubits, wherein each set of entangled qubits are not entangled with qubits in any of the other sets of entangled qubits. Some embodiments include reading the states of qubits in each set of qubits, wherein the signals applied to the qubits in the second set of qubits are determined by weighted linear combinations of the states of the qubits in each other set of qubits. In some embodiments, the weights are based on interaction values between the qubits in the first set of qubits and the qubits in the second set of qubits in a final Hamiltonian whose eigenvalue solution is desired.

Some embodiments include:
initializing the first and second sets of qubits in initial known states based on an initial Hamiltonian;
adiabatically evolving the first set of qubits and the second set of qubits towards the final Hamiltonian;
during said adiabatic evolution, applying said signals to the second set of qubits;
once the final Hamiltonian is achieved, reading states of each of the first and second set of qubits; and
outputting the states as the eigenvalue solution to the final Hamiltonian.

Some embodiments further include:
reading a state of each of the qubits in the second set; and
during said adiabatic evolution, applying a second set of signals to the qubits in the first set, wherein each signal in the second set of signals is determined by second weighted combinations of the states of the qubits in the second set, wherein the second weights are based on interaction values between the first set of qubits and the second set of qubits in the final Hamiltonian.

Still other embodiments disclosed herein include a method of computation, comprising:
emulating a first set of entangled qubits in a classical computer;
emulating a second set of entangled qubits in the classical computer;
simulating, in the classical computer, a plurality of external fields acting on the qubits, wherein the external fields acting on each qubit in the first set is based on the mean value of each emulated qubit in the second set and the external fields acting each qubit in the second set is based on the mean value of each emulated qubit in the first set;
iterating the emulated qubits with applied simulated external fields to simulate an adiabatic evolution of the qubits from an initial Hamiltonian to a final Hamiltonian whose eigenvalue solution is desired; and
outputting final values of the qubits after the iteration is complete.

DETAILED DESCRIPTION OF THE PREFERRED EMBODIMENT

Described herein are several new systems and uses of systems operating in what is termed herein as the "Poised Realm." By "Poised Realm," it is meant a physical system that does not exhibit fully quantum behavior nor exhibits fully classical behavior. In this sense, the system is "poised", or even can "hover" between the quantum and classical worlds. By Poised Realm, we mean any physical means or procedure to achieve such a system poised between quantum and classical behavior, including as bounding limits, fully quantum coherent behavior and fully classical behavior.

In one characterization of the Poised Realm, we use two independent features of, without loss of generality, open quantum systems. The degree of decoherence and/or recoherence is one feature. In addition to their quantum, decohering, recohering, or classical behavior, physical systems may also be classified according to the degree of order or chaotic behavior that they exhibit along an order-criticality-chaos spectrum. Systems within the Poised Realm may be characterized by any degree of order along this spectrum. In some embodiments, the physical systems described herein do not exhibit full order or chaos and are thus also "poised" between order and chaos. Below we describe new theorems which establish that WITHIN the poised realm itself, ie not classical, critical poised realm systems in the presence of decoherence lose coherence most slowly, that is in a power law fashion, while ordered or chaotic Poised Realm systems lose coherence exponentially, hence decohere much faster in the absence of recoherence.

As used herein, "recoherence" refers to a system entering again into a superposition state after it once lost its coherence. The term "recoherence" commonly refers to the re-emergence of some initial quantum state during coherent quantum evolution, which is different from the meaning used herein.

Figure 1:
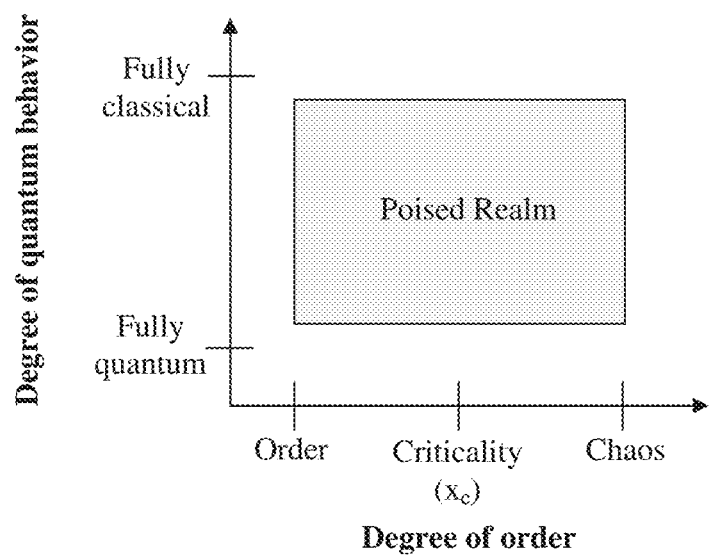
FIG. 1 is graph depicting the boundaries of the Poised Realm.

Thus in at least one characterization of the Poised Realm, the Poised Realm may be illustrated by a two-dimensional coordinate system having as its y-axis (the vertical) the degree of quantum behavior, stretching from fully quantum behavior at the "origin" to fully classical behavior "up" the y axis, typically by decoherence and movement down the Y axis toward quantum behavior via recoherence, and on the x-axis (the horizontal) the degree of order, stretching from full order to full chaos (see FIG. 1). The area on the graph between fully quantum and fully classical behavior is at least one definition of the "Poised Realm." The y axis in FIG. 1 can be infinite in that classical behavior in some circumstances, in particular via increasing quantum decoherence, can be approached as closely as wished, i.e., achieved "For All Practical Purposes" (FAPP).

Thus, as used herein, a "fully classical" system or a system that is "classical for all practical purposes" is a probabilistic mixture of single amplitudes. A "fully quantum" system is one in which all or at least one of quantum degrees of freedom comprise a superposition of possibility waves. Other possibilities or amplitudes may have lost superposition and be comprised by one "pure state" amplitude or a set of pure state amplitudes called a "mixed state". These terms may be understood by the classical double slit experiment, where photons in coherent fully quantum states exhibit an interference pattern. If a detector is used at one or more of the slits, interaction with the detector causes the photons' wave functions to collapse such that they are no longer quantum coherent (i.e., they exhibit classical behavior), resulting in loss of the interference pattern.

Degree of Order

The system in general can be described by its Hamiltonian H. Classical trajectories of the system can be calculated from the Hamiltonian via solving its Hamiltonian equations. Quantization of the Hamiltonian results in the Hamiltonian operator $\hat{H}$, which fully describes the system's quantum dynamics via the Schrodinger equation. The Hamiltonian may depend on several parameters of the system. By changing the parameters of the system we can change the form of its Hamiltonian. Later we refer to this as "changing the Hamiltonian".

By changing the Hamiltonian we can change the degree of chaos in the system. Degree of chaos of trajectories can be characterized by their Lyapunov exponents. One can assign a Lyapunov exponent to each point in the phase space by calculating the Lyapunov exponent of the trajectory initiated in the point. In the phase space one can find connected areas where the Lyapunov exponent is positive and characterized by the same value within the patch. These chaotic patches are separated by regular areas, where the Lyapunov exponent is zero. The degree of chaos in the system can be characterized by the relative proportion of the volume of the chaotic areas in the phase space. If no chaos is present, the proportion is zero. If the system is chaotic for almost all initial conditions the proportion is 1. The position of the system on the x-axis (the horizontal) is this ratio. Usually changing a parameter of the Hamiltonian such a way that its Hamiltonian equations become more nonlinear increases the degree of chaos and moves the system to the right on the x-axis.

In the process of moving the system to the right on the x-axis new chaotic areas emerge, the size of the existing areas increase and separation of some of the existing chaotic areas disappear. There is a critical point on the x-axis, $x_c$, below which the chaotic areas form separated patches in the phase space. Above the critical point the chaotic areas coalesce and form a giant connected component. Below the critical point chaotic trajectories are confined within their chaotic area in the phase space. Above the critical point chaotic trajectories can diffuse globally in the phase space.

In the critical point the Lyapunov exponent for the globally connected chaotic area is zero and it goes through a second order phase transition in the neighborhood of the critical point. It is zero $\lambda_0(x_c)=0$ below the critical point $x<x_c$ and shows power law scaling $\lambda_0(x) \sim (x-x_c)^\beta$ above $x>x_c$ with some positive exponent $\beta$.

Some quantum systems, such as spin systems are defined only with their Hamilton operator and their classical Hamiltonian cannot be defined. In such systems the x-axis and its critical point can be defined purely quantum mechanically. In the pure ordered regime the phase space motion happens on a torus. Quantum mechanically it is a separable system and its eigenenergies correspond to the quantization of its tori. The energy eigenvalues of the system follow Poissonian distribution. The nearest neighbor level spacing distribution is exponential:

$$p_P(s) = \exp(-s)$$

where $s_n = (E_{n+1} - E_n)/\Delta(E_n)$ is the level spacing measured in the units of local mean level spacing $\Delta(E)$ at energy E. In the purely chaotic system the energy level statistics of the system can be described by Random Matrix Theory (RMT) and the level spacing follows approximately the Wigner surmise:

$$p_w(s) = \frac{\pi s}{2} \exp(-\pi s^2/4)$$

These limiting cases correspond to the values 0 and 1 on the x-axis respectively. In an intermediate situation, where the system is neither fully ordered or fully chaotic, the quantity $$x = \frac{A - A_p}{A_w - A_p}$$

can serve as the x-coordinate where $$A_p = \int_2^\infty p_p(s), \; A_w = \int_2^\infty p_w(s),$$

and the quantity A is calculated from the actual level spacing of the system $$A = \int_2^\infty p(s).$$

In the above mentioned quantum systems the criticality can be defined in a purely quantum mechanical way. In the ordered region the eigenfunctions of the Hamilton operator are localized in configuration space. In the chaotic region the eigenfunctions are delocalized and extended over the configuration space of the entire system. The critical value $x_c$ separates these two behaviors. The level spacing statistics in the critical point can be well approximated by the semi-Poissonian distribution p(s)=4s exp(-2s).

Systems in nature don't exist in full separation. They are coupled to their environment. Coupling a low dimensional quantum system to an infinite degree environment exert random forces on the system. The system loses its quantum coherence as a result. The environment-system coupling can be described by the Hamilton operator $\hat{H}=\hat{H}_s+\hat{H}_{e-s}+\hat{H}_e$, where the Hamiltonian operators correspond to the system $\hat{H}_s$, to the environment-system coupling $\hat{H}_{e-s}$ and to the environment $\hat{H}_e$. The strength of the external forces causing decoherence is measured by the variance of system-environment coupling averaged over the states of the environment $\Gamma^2 \langle \hat{H}_{e-s}^2 \rangle$. The position of the system on the y-axis (the vertical) is the ratio of $\Gamma$ and the average level spacing $\Delta(E)$ of the system $\hat{H}_s$.

Some embodiments include modulating or controlling the degree of order of a physical system (i.e., moving along the x-axis of FIG. 1). Some such embodiments include engineering a system to have a desired degree of order. In various embodiments, the following describes, without limitation, three methods for controlling the degree of order in a system.

1) Position on the x-axis due to the Hamiltonian of a system. In general, altering the Hamiltonian of the system by any means may alter its position on the x axis. More specifically, due to the dynamics of the Poised Realm system ITSELF, the classical Hamiltonian of the system can change, changing its position on the x-axis statically or, as we will see, dynamically, as one non-limiting example, from order to criticality to chaos and back.

Classical dynamical systems are often describable as flows on a Hamiltonian. Such flows can, for example, and without limitation, describe most classical physical dynamical systems. A periodic pendulum is a simple example of a system in the ordered classical regime describable by a Hamiltonian. Analogous quantum oscillators are also in the ordered regime. Other Hamiltonians can be critical or chaotic classically.

The dynamical behaviors of such classical systems can be ordered on the x-axis from ordered to critical to chaotic, by means of diverse measures of their dynamical behavior. Several such methods are known in the art. Without limitation, a preferred method to array classical Hamiltonian dynamical systems on the x-axis is by measuring their average Lyapunov exponent, as is known in the art, averaged over the time behavior for short times and from multiple initial states of the system in question. The Lyapunov exponent measures whether nearby trajectories diverge, (chaos), converge, (order), or flow parallel to one another, (criticality), in state space. Account can be taken of the attractor basin sizes, should the classical system have both at least one attractor and may have more than one attractor, each "draining a basin of attraction." Then, typically one measures the Lyapunov exponent on each attractor and weights these by the basin sizes of that attractor, averaged over all attractors, to get a global measure of position on the x-axis. Alternatively, the Hamiltonian system may have no attractor, as in classical statistical mechanics and exhibit ergodic behavior, and satisfy the Louiville equation, as is known in the art.

Thus, classical systems can be moved on the x-axis by "tuning" their Hamiltonians. As we will see, in the Poised Realm quantum degrees of freedom can become classical or classical for all practical purposes, FAPP, and thereby alter the classical Hamiltonian of the system, so the very dynamics of Poised Realm systems can move the classical degrees of freedom from order to criticality to chaos and back.

2) Supression of decoherence. Systems in the poised realm can be characterized by their position on the x and y axes in terms of chaos-order and the strength of the coupling to the environment. Depending on their position they are exposed to the decoherence caused by the environment. Quantum systems can be described by their density matrices ($\rho_{nm}$) as it is known to the art. Theoretically, the decay of coherence can be characterized by the speed the off diagonal elements (n≠m) of the density matrix die out $\rho_{nm} \sim e^{-t/\tau_c}$; where $\tau_c$ is the coherence time. An overall measure of the speed of the loss of the coherence is the entropy production in the system. In practice the production of the standard Shannon ($S_1 = -\text{Tr}[\rho \log \rho]$) entropy and the more easily computable Renyi entropy ($S_2 = \log \text{Tr}[\rho^2]$) are used.

The exponential time dependence of the off-diagonal elements of the density matrix and the entropy production rate are closely related:

$$\frac{dS_{1or2}}{dt} \sim \frac{1}{\tau_c}$$

Entropy production due to decoherence is related to the dynamical properties of the system. It has been shown via semiclassical arguments and direct simulations that after an initial transient the entropy production rate is related to the Kolmogorov-Sinai entropy ($h_{KS}$) of the dynamical system:

$$\frac{dS_1}{dt} \sim h_{KS} = \sum_i \lambda_i^+$$

which is in turn the sum of the positive Lyapunov exponents $\lambda_i^+$ characterizing the exponential divergence of chaotic trajectories. Entropy production becomes slow when the largest Lyapunov exponent and the Kolmogorov-Sinai entropy of a system vanishes ($h_{KS} \approx \lambda_o \to 0$). In this case the coherence time becomes formally infinite $T_c \to \infty$ indicating a slower than exponential decay of coherence in the system, where the off diagonal elements of the density matrix stay finite or die out only in an algebraic way $$\rho_{nm}(t) \sim \frac{1}{t^\alpha}$$

where α is the exponent of the power law decay.

The zero entropy production state emerges in mechanical systems at the border of the onset of global chaos $x_c$ of the classical counterpart of the system. In quantum systems without classical counterpart the transition happens also at $x_c$, where $x_c$ is now defined in terms of the critical level spacing p(s)=4s exp(−2s).

Suppose, we have a parameter ε of a mechanical system which characterizes its transition from integrability to chaos:

$H = H_0 + \varepsilon H_1$.

Here $H_0$ is the Hamiltonian of an integrable system. Classically and quantum mechanically it is a solvable system. Classically it can be described by action-angle variables and it does only simple oscillations in the angle variables. The phase space motion happens on a torus. Quantum mechanically it is a separable system and its eigenenergies correspond to the quantization of its tori. The energy eigenvalues of the system are random and follow a Poissonian distribution. The nearest neighbor level spacing distribution is exponential $p(s) = \exp(-s)$;

where $s_n = (E_{n+1} - E_n)/\Delta(E_n)$ is the level spacing measured in the units of local mean level spacing $\Delta(E)$ at energy E. The Hamiltonian $H_1$ is a perturbation. When ε≠0 the system is no longer integrable classically and no longer separable quantum mechanically. At a given small ε, the Kolmogorov-Arnold-Moser (KAM) theory describes the system. The perturbation breaks up some of the tori in the phasespace and chaotic diffusion emerges localized between unbroken, so called KAM tori. Chaotic regions are localized in small patches in the phasespace surrounded by regular parts represented by the KAM tori. At a given critical ε KAM tori separating the system gets broken and the chaotic patches merge into a single large chaotic sea. Above the transition $\varepsilon > \varepsilon_c$, the system is fully chaotic characterized by a positive largest Lyapunov exponent $\lambda_o > 0$. The energy level statistics of the system can be described by Random Matrix Theory (RMT) and the level spacing follows the Wigner surmise:

$$p(s) = \frac{\pi s}{2} \exp(-\pi s^2/4).$$

For our purposes the most important region is $\varepsilon = \varepsilon_c$. In the transition point the Lyapunov exponent is zero and it goes through a second order phase transition in the neighborhood of the critical point. It is zero $\lambda_o(\varepsilon) = 0$ below the critical point $\varepsilon < \varepsilon_c$ and shows power law scaling $\lambda_o(\varepsilon) \sim (\varepsilon - \varepsilon_c)^\beta$ above $\varepsilon > \varepsilon_c$ with some positive exponent. At the transition point the level statistics is a special universal statistics called semi-Poissonian:

$p(s) = 4s \exp(-2s)$.

In this transition point where entropy production is zero, the system is the most robust against decoherence and a system can stay coherent for an anomalously long time in this point. Below the transition point the system is localized and no global transport is possible. Although entropy production is low in this region the system is not suitable for complex transport and also decoherence is strong as each separate localized patch in the phase-space supports a localized wave function quantum mechanically. Each patch is affected by decoherence in a direct way and coherence is lost exponentially rapidly. Far above the transition point strong chaos induces mixing and entropy production which causes rapid decoherence. Near the transition point from above, however metastable states are formed and the wave functions show critical fractal structure. The complex geometry and spatial structure of these transitional states is able to avoid the effects of decoherence most effectively.

The transition described above is much more general than just the integrable-chaotic transition. An example is the metal-insulator transition point. Such localization-global transport (conductance) transition is present when we add static random potential to a clean and perfectly conducting lattice. At a critical level of the added random potential the system stops conducting and the system becomes insulating due to Anderson localization of its wave-function. In this system the control parameter ε is the variance of the random potential. The energy level statistics of the metallic system is described by RMT and the localized states produce Poissonian statistics. In the transition point semi-Poissonian statistics emerges. The same transition can occur also in the conducting properties of random networks (graphs). There the localization-global conductance transition occurs at the percolation threshold, where the giant component of the network emerges. Finally, the same transition can be seen in finite quantum graphs by changing its geometry in specific ways.

In all these systems the metal-insulator critical point is characterized by a fractal structure of the wave function similar to those in the chaos-integrability transition. Moreover, the equivalence of the metal-insulator and chaos-integrability transitions has also been proven analytically. Therefore it seems reasonable to claim that the suppression of the decoherence is also a universal feature of the critical point of the metal-insulator transition. We can suppress decoherence and keep our system coherent for an anomalously long time if we deliberately keep it in the transition point. We call this state the Poised Realm Critical.

Experimentally, the Poised Realm Critical state can be identified by measuring the decay of coherence in the system. In a non-critical system the coherence decay is exponential in time. The Poised Realm state is signaled by a slow, typically power law decay of coherence. State of the art coherence decay measurements are based on various echo measurements depending on the system studied. This includes spin echo, neutron spin echo, and photon echo.

3) Position on the x-axis is tunable by the detailed and/or statistical structure of quantum networks and graphs. As known in the art, quantum graphs and quantum networks may be used to model real systems such nano-structures. During dynamical behavior of a Poised Realm system, the structure of a quantum network corresponding to a real system can change, altering position on the x-axis.

Figure 2:
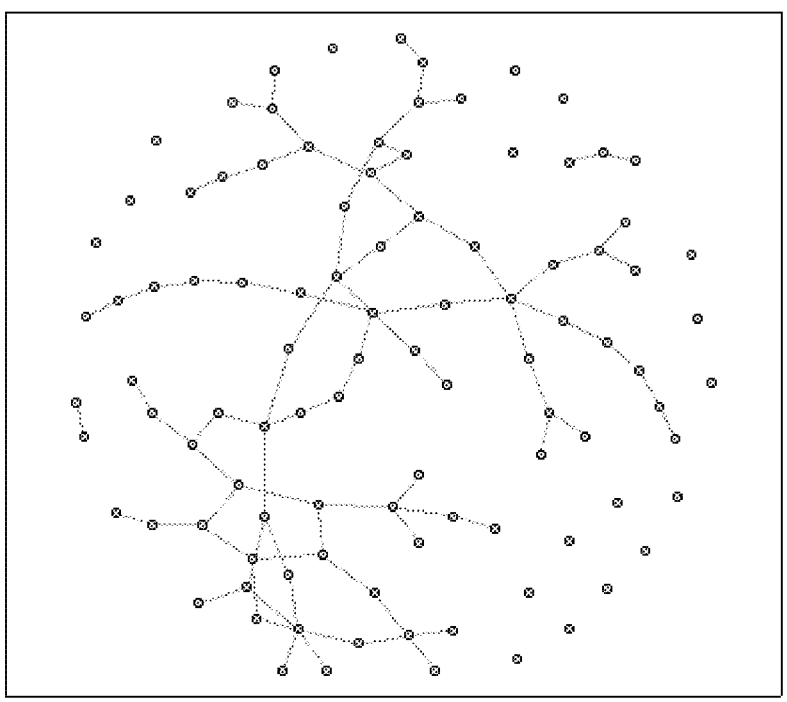
FIG. 2 is a graph depicting an Erdos-Renyi Random Graph with Giant Component.

It is convenient to start with the famous Erdos Renyi (ER) Random Graphs as the simplest possible examples of quantum networks. An ER graph is "grown" by starting with a set of N disconnected nodes. Random pairs of nodes are chosen, and joined by a "line" or "link". This process is iterated, so that at any point, some ratio of links/nodes exists. ER graphs are extraordinary and have driven much research. Most importantly, they exhibit a first order phase transition from essentially disconnected tree "subgraphs" to a single "Giant Component." Define a "cluster" as a set of interconnected nodes. When the ratio of links/nodes is less than 0.5, the graph consists of isolated pieces. As 0.5 is approached, initially small tree-like structures become larger and larger. At link/node ratio 0.5, when the number of ends of links equals the number of nodes, the phase transition to a Giant Component occurs. Intuitively once there are a few very large tree-like graphs for an arc/node ratio a bit below 0.5, a few randomly connected nodes will tie all or most of the large tree-like nodes into the Giant Component (see FIG. 2).

Amazing things happen at this phase transition. Not only does the giant component come to exist, but for the first time loops of all lengths emerge in the giant component.

At the critical ratio of links/nodes, 0.5, the ER graph is said to be "critical". But many nodes are still not connected.

As the ratio of links/nodes increases past 0.5 two major things happen. Isolated nodes and small trees are tied into an enlarging Giant Component. Second, the Giant Component becomes increasingly richly cross connected, so average <k> rises.

Such graphs can be considered static quantum networks. Their structure is given by an Adjacency N×N matrix, with a 1 in matrix element i,j if there is a connection between nodes i and j. By symmetry, the j,i matrix element is also 1. Otherwise, for all pairs that are not joined by a line, the matrix element in the Adjacency matrix is 0.

Figure 3:
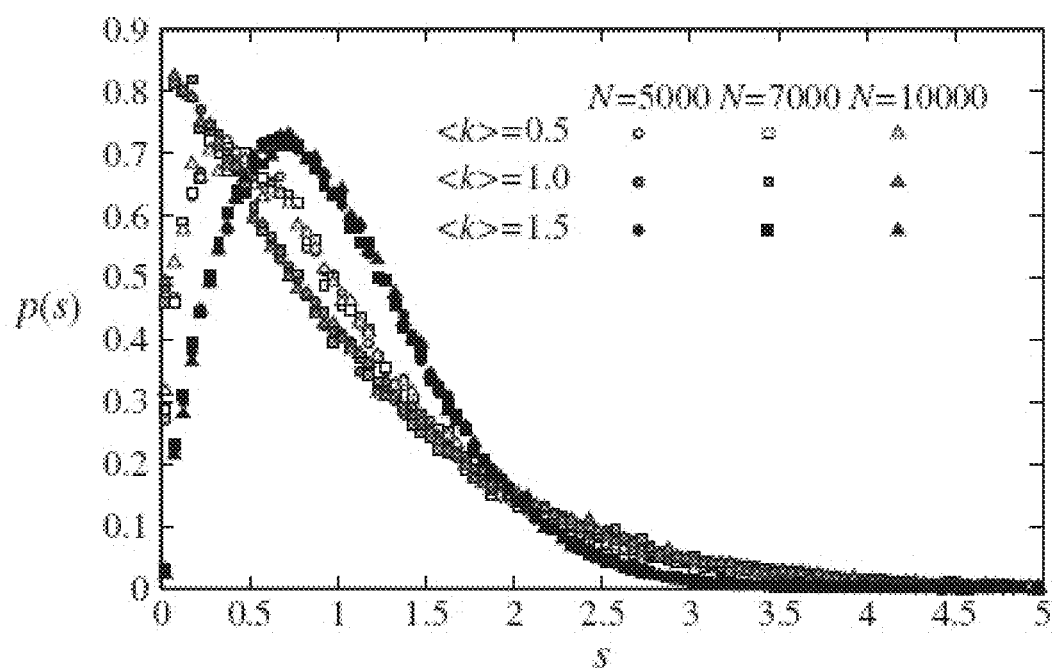
FIG. 3 is a graph depicting the energy level spacing for Erdos-Renyi random graphs.

The eigen values of the Adjacency matrix give the energy levels of the quantum network. From this one can compute the "energy jumps" between all pairs of energy levels, and from this the distribution of energy jumps, or quanta sizes, in the ER subcritical, critical, or supracritical="chaotic" quantum networks FIG. 3 shows the spectrum of critical, and 2 successively more supracritical networks, mean ratio lines/nodes=<k>=0.5, 1.0 and 1.5. All have giant components which, since they contain most of the nodes, dominate the eigen value spectrum.

These results show that in ER critical and supracritical graphs, position on the x-axis, critical or chaotic, can be attained by modification of the quantum network structure.

The quantum networks above are structures, realizable, for example, by networks of carbon nanotubes capable of quantum behavior. Molecular systems can also be regarded as quantum networks. Below we discuss two generic models of quantum degrees of freedom: quantum rotors and quantum oscillators. It will be clear to those of ordinary skill in the art that arbitrary graphs can be endowed with quantum oscillators and/or rotors at, without limitation, some or all nodes, and their quantum and order-critical-chaos behaviors studied. Without limitation, quantum oscillators can be coupled in arbitrary topologies to one another by interactions (for example spring-like harmonic interactions). To date, most work has focused, as we will describe, on single "kicked" quantum rotors, or two coupled quantum oscillators coupled by a spring and/or coupled to a quantum oscillator "heat bath," as is known in the art. These models are fully extendable to arbitrary networks, as above, as the quantum system in an arbitrary quantum environment. As discussed below, these models, in particular, networks, are suited to model chemical molecules, will be applied to the evaluation of candidate drugs and the behaviors of nanotube structures.

As noted above, one method of controlling position on the x-axis is to change the network structure. For example in our application of these ideas to drug design and nano-technology design, a given network can model a molecule. By adducting to it another molecule, say by hydrogen bonds or other non-covalent interactions, the graph structure of the new network can be made less than critical, critical, or more supracritical.

We note that networks of more arbitrary structures can be made with carbon nanotubes or other materials, than can be made with atoms such as carbon, hydrogen, nitrogen, oxygen, phosphorus, and sulfur, due to the bonding properties of these specific atoms.

Controlling the Topology of the Quantum Networks Via Proximity of the Nodes

Consider as a non-limiting example a set of chromophores, parts of molecules or independent molecules. Electron exchange is one means of linking the chromophores, as a non-limiting example.

The details of this interaction depend upon the detailed positions of the chromophores. However, in general, if they are sufficiently close, so each chromophore can communicate with many neighbors, many closed quantum loops will exist and the quantum network will be supracritical, hence "chaotic". If further apart, the quantum network will be less connected, and critical or subcritical, moving thereby on the x-axis. As we see below, chromophores bound to the membrane of a liposome can be made more or less chaotic on the x-axis by subjecting the liposome to hypertonic or hypotonic media that shrink or swell the liposome.

As used herein, a generalized "chromophore" refers to any quantum network of interacting elements.

In general, these quantum networks may be on rigid structures such as nanotech devices (e.g, carbon nanotube structures). Or they might be inside or outside or both of a liposome, made as is known in the art, as a bilipid double membrane hollow vesicle, with the chromophores anchored to the bilipid double membrane via covalent bonding to beta barrel proteins spanning such bilipid layers. The density per liposome of generalized or specific chromophores in the general sense used here can be tuned through a wide range. As described later in the section on embodied algorithmic or non-algorithmic trans-Turing Machine quantum-Poised Realm-classical information processing systems, which might be nanostructures or liposomes or other vehicles, liposomes can be constructed from lipids in water containing the beta barrel proteins with attached chromophores. One expects a random distribution of chromophores inside and outside the liposome membrane, allowing such a structure to receive quantum information via the external chromophores and internal chromophores where light, or other quantum degrees of freedom without limitation, reaches to and across the membrane. The set of all the chromophores form a quantum graph that, together with the liposome and aqueous interior with chosen concentrations of ions and other small and larger molecules, will behave in open quantum, Poised Realm, and classical ways, as described below, for example without limitation via repeated decoherence and recoherence of quantum degrees of freedom to classicity, which degrees of freedom when classical, or classical (for all practical purposes, FAPP), will alter both the classical Hamiltonian of the system, and thereby also alter the Hamiltonian of the quantum degrees of freedom. Similarly the recoherence of a classical degree of freedom, as discussed below, will alter both the classical and quantum Hamiltonians of the system, hence the total behavior of the coupled classical and quantum system over time. These facts are useful in Trans-Turing systems, below.

We also note here that quantum measurement can occur in the Poised Realm, in the presence of decoherence and recoherence. Measurement may be achieved, without limitation, by any means. As a central non-limiting example, the classical degrees of freedom of a system above, as in our Trans-Turing systems below, themselves constitute part or all of the quantum measuring system which can measure, in some basis, one or more of the quantum degrees of freedom of the system.

4) Position on the x axis may be controlled by pulsed stimulation. A third method to control position on the x-axis (i.e., degree of order), is by pulsed stimulation. This method may be modeled by a kicked quantum rotor. Basically a quantum rotor is a quantization of a classical rotor on a frictionless stand that is spinning with some frequency. If the classical rotor is tapped with "Dirac delta" inputs of momentum gently, it remains in the ordered regime, hence left on the x-axis. As it is kicked harder and harder, it moves out on the x-axis, becomes critical, then chaotic. The same holds for quantum rotors as we describe below in detail. In the quantum case, the quantum rotor degree of freedom is kicked with Dirac delta laser light momentum kicks where the intensity, "K," of the kick can be increased, driving the rotor from order to chaos. This characteristic is expected to extend to systems having arbitrary Hamiltonians. Thus, one embodiment includes modifying the state of order or chaos of a system by stimulating the system pulsed light.

It is expected that quantum rotors or other Hamiltonians kicked to ordered, critical or chaotic states will exhibit different quantum energy level distributions. Thus, measurement of such distributions (e.g., through spectral analysis) demonstrates the degree of order of such a system. Thus we can readily test for position on the x-axis.

For real quantum systems, an issue is at what light frequency to kick the quantum system. In one embodiment, the center of one or many of the absorption/emission band(s) of that quantum degree of freedom or a set of quantum degrees of freedom is used for the stimulation.

Degree of Quantum Behavior

For actual physical systems, which can be modeled with quantum network structures, the molecular topology of the system can tune the decoherence rates, and thus movement on the y-axis, in the processes engendered by the system. The electronic energy transfer in chlorophyll is the best example of such a system with both theoretical and experimental results showing long-lived quantum coherence in an intrinsically noisy cellular environment. Hence the structure of chlorophyll may play a major role in resistance to decoherence.

Movement from quantum to classical via decoherence. Decoherence is a well established phenomenon and the current favored explanation of the transition from the quantum to the classical worlds. In quantum mechanics, the signature interference pattern due to constructive and destructive interference can only occur if all the phase information is present in the quantum system. But in an open quantum system, phase information can be lost from the quantum system to the environment in an irretrievable way. As this happens, the capacity for interference patterns in the quantum system decays.

There are at least two 'as if' models of decoherence. The best established is the "Lindblad operator", which allows the off diagonal elements of the density matrix of the system containing the phase information to decay.

A second model of decoherence makes use of a random walk process called either a Weiner process, σWdt. In a Weiner random walk process, the Weiner noise term is a random Gaussian variable with mean 0 and a variance, σ. The larger σ is, the larger is the average random phase step on the orbit in the complex plane of the quantum degree of freedom, such as the quantum rotor.

We have focused in our simulations of the kicked quantum rotor on the Weiner process, but have also used the Lindblad operator. In the Weiner process, a variance of 0, σ=0, is "no coherence," hence quantum on the y-axis. As σ increases, the noise increases, and the rate of decoherence increases.

In the Quantum Zeno effect, demonstrated experimentally, a quantum degree of freedom is measured very frequently. Each time it is measured, by von Neumann, it falls to a single amplitude, or eigen state. It then slowly, quadratically in time, leaves that quantum eigen state and "flowers" to populate nearby and then more distant amplitudes of that quantum degree of freedom. However, if it is frequently measured, it is almost certainly "trapped" in its initial quantum eigen state, and the time evolution of the Schrodinger equation is stopped. As it flowers to nearby amplitudes it becomes a superposition state again, moving up the y-axis. So frequent measurements, tunable, can keep a quantum system near classical or somewhat quantum because only a small number of amplitudes have "flowered," hence control position on the y-axis.

Passing from classical or classical FAPP to more coherent or fully coherent, i.e., down the y axis. One embodiment includes driving a system to be more coherent including driving a classical system back to quantum. One embodiment includes driving a classical system into the Poised Realm.

We consider a time independent (autonomous) quantum system described by the Hamiltonian H under the action of a time dependent external potential U(x; t). We can separate the coherent and temporally random parts U(x; t)=$V_r$(x; t)+$V_c$(x; t). The random part causes decoherence while the coherent part causes re-coherence in the system. Assuming that the random part is uncorrelated in time and using Ito's rule we can get the time evolution of the averaged density matrix $$\partial_t \zeta(x, x', t) = -\frac{i}{\hbar}[\hat{H} + \hat{V}c, \zeta(x, x', t)] - \frac{1}{\hbar^2}\Gamma(x, x')\zeta(x, x', t),$$

where $\tau(x,x')$=C (x; x)+C(x', x')−2C(x, x') and $<V_r(x,t')>$=C (x,x') δ(t−t') is the temporal autocorrelation of the random potential at different spatial sites x and x'. In most relevant situations a simple discrete Hamiltonian can describe the system with matrix elements $H_{nm}$ and the simplest delta correlated noise can be assumed $C_{nm}$=C$\delta_{nm}$ and $\Gamma_{nm}$=Γ(1−$\delta_{nm}$). The coherent external potential, which can come from laser pulses or any other coherent electromagnetic source, can be reasonably modeled with a sequence of sharp kicks $\hat{V}_c$(x; t)=$\Sigma_n$V(x)T δ(t−nT) at times nT.

In absence of the coherent part the evolution of the density matrix is described by $$\partial_t \rho_{nm} = -\frac{i}{\hbar}\sum_k \left(\hat{H}_{nk}\rho_{kn} - \rho_{nk}H_{km}\right) - \frac{\Gamma}{\hbar^2}(1-\delta_{nm})\rho_{nm}.$$

Decoherence kills quantum superposition states represented by the off-diagonal elements of the density matrix. The density matrix settles to the diagonal form $\rho_{nm}$=$\delta_{nm}P_n$, where $P_n$ is the classical probability of finding the system in state n. The characteristic decay time is $h^2/\Gamma$~10-100 femtoseconds. The coherent part is able to re-create superposition states. The density matrix before and after the coherent kick is $$\rho^+_{nm} = \sum_{n'm'} U_{nn'} U^*_{m'm} \rho^-_{n'm'}$$

where the unitary matrix $U=\exp(i\hat{V}_c T/h)$ describes the action of the kick on the wave function.

Even if the density matrix is diagonal before the kick $Q^-_{nm}=\delta_{nm}P_n$ it becomes non-diagonal after the kick $$\rho^+_{nm} = \sum_k U_{nk} U^*_{km} P_k,$$

indicating the presence of superposition states. Kicking the system repeatedly can repair the coherence lost during time evolution and keep the system levitating at the border of the 'realms' of quantum and classic. The interplay of the coherent kicks and decoherence determines the speed of the loss of coherence in the system.

Evidence of that systems can be driven to more quantum behavior include the following:

1) In the Zeno Effect, the system is trapped in one eigen state, hence classical during the interval before remeasurement. If not remeasured, the system again flowers multiple quantum amplitudes quadratically in time. One means by which such reemergence of quantum amplitudes happens is in a system which is a quantization of a classical chaotic dynamical system. One of the quantum amplitudes of the localized quantum behaviors of the quantum system is measured, causing the system to collapse to a single possibility via the Born Rule and is briefly Quantum Zeno Effect "trapped" in the eigenstate. This amplitude emerges quadratically in time to repopulate other quantum amplitudes with finite moduli.

2) A second means known in the art to regain quantum coherent behavior concerns quantum entangled degrees of freedom in a quantum squeezed state. For specific systems, quantum entanglement can undergo "Sudden Death", can undergo No Death, and can undergo Sudden Death and Revival. Such Revival is a revival of coherent entangled quantum behavior from far in the classical region (FAPP or entirely classical). We incorporate by reference, "Entanglement dynamics during decoherence", J. P. Paz, A. J. Roncaglia, Quantum Inf Process (2009) 8 535-548 in it's entirety. We also incorporate by reference in their entirety "Entanglement and intra-molecular cooling in biological system?—A quantum thermodynamic perspective." H. J. Briegel and S. Popescu Phys arXhiv 0806,4552V2 [QUANT-PH] 5 Oct. 2009 and "Dynamic entanglement is oscillating molecules", J. Cai, S. Popescu and H. J. Briegel arXhiv: 0809.4906v1 [quant ph] 29 Sep. 2008. The last two articles computationally demonstrate and suggest recurrent passage from coherent entanglement to classical behavior and back. The last paper posits conformational changes of a biomolecule induced by interaction of some other chemical at an allosteric site.

3) A third means known in the art to regain coherence is given by the Shor Theorem, which states that in a quantum computer with entangled quantum degrees of freedom, the quantum system can be quantum measured using quantum degrees of freedom not part of the qubit calculation. Information can be injected from outside the quantum computer that restores quantum coherent behavior to the decohering quantum degrees of freedom, i.e., qubits.

4) A fourth means that induces increased coherence in a quantum or partially quantum, partially decoherent, and perhaps partially fully decoherent system almost certainly occurs in chlorophyll wrapped by its evolved "antenna protein." At 77 degrees K., the expected time scale for decoherence is on the order of a femtosecond. The chlorophyll molecule, having been excited by absorption of a photon by an electron, remains in the quantum coherent (or largely coherent) state for at least 700 femtoseconds.

It is believed that this astonishingly long lived coherent state is due to the antenna protein. This can be experimentally verified by use of mutant antenna proteins, and this has been done with the antenna protein and its mutants for a bacterial rhodopsin molecule, where loss of coherence occurs with mutant antenna proteins. Long lived quantum coherence may also be partially due to the quantum graph structure of chlorophyll.

It may be that the antenna protein entirely blocks any decoherence to the full environment of the chlorophyll molecule. It is more likely that the antenna protein, filled with chromophores, acts on the chlorophyll molecule by driving it with photons in a physically realized version of some type of Shor theorem, to inject information into the chlorophyll and sustain or restore coherence to the chlorophyll molecule. But restoring coherence means that in physical reality, the antenna protein can increase coherence in quantum degrees of freedom of the chlorophyll molecule. The topology of the chlorophyll molecule may play a role either in its resistance to decoherence, or ease of recoherence via input from the antenna protein.

Chlorophyll and its antenna protein is a probable example of a fourth general means to drive a system from classical due to decoherence and phase randomization as above, by kicking the quantum degree of freedom at exactly the natural frequency of any one or a plurality or all of its quantum amplitudes. Think of a classical rotor whose phase is being randomized by modest sized hammer kicks at frequencies that are irrational with respect to its natural frequency. Now hit it with a hammer of tunable size at its natural rotation frequency. You will tend to or will overcome the modest sized hammer irrational "noise" taps and resynchronize the classical rotor. In the same way, consider a quantum degree of freedom with a sharp band spectrum. Each band is the exact frequency of light that must hit that quantum degree of freedom with high intensity to resynchronize its phase and drive the classical, decoherent degree of freedom down the y-axis through the Poised Realm toward fully quantum behavior. Almost certainly, the antenna protein chromophores are doing this, a hypothesis which is testable by mutating the chromophores and showing that sustained coherence of chlorophyll decreases then correlating the decreased coherence with a change in the emission spectra of the chromophores on the antenna protein with respect to the absorption/emission spectrum of chlorophyll. This experiment as been done with a bacterial rhodopsin and its antenna protein with exactly the above result, although matching to the emission frequencies of the antenna protein and absorption bands of chlorophyll have not, to our knowledge, been examined.

Additional data has shown that, in a spin bath environment, a quantum system can exhibit partial decoherence that levels off with medium coherence, in the Poised Realm, where coherent behavior propagating a finite number of coherent amplitudes persists indefinitely. If the system is started with less coherence, ie "more classical" in the Poised Realm, it recoheres to the same intermediate level, propagating a finite number of quantum amplitudes coherently. Such stable propagating amplitudes that persist despite decoherence are useful in quantum computation.

As discussed above regarding the degree of order, decoherence can be suppressed and the system kept coherent for an anomalously long time if it is deliberately kept at the Poised Realm critical transition point. Within the poised realm, ordered and chaotic behavior is associated with rapid exponential decoherence. In sharp contrast, along a critical locus in the poised realm roughly paralleling the y axis and terminating at criticality on the x axis, poised realm systems decohere much more slowly, in a power law, not exponential decay of coherence. Thus, within the poised realm, criticality preserves coherence better than other positions within the poised realm.

Measuring decoherence and recoherence experimentally in real quantum systems. There is a very convenient measure of decoherence. A dilute gas of a single atomic species, e.g., hydrogen, has very sharp absorption and emission bands, forming its spectrum. In general, as decoherence sets in, these bands become wider. Thus, the width of a band is a convenient measure of the decoherence status of that amplitude of the quantum system, which is easy to measure with standard spectrography.

Recoherence can be seen, for example due to driving with light whose wavelength is at the center of a broadened band, by progressive narrowing of that band. Conversely decoherence and its rate can be measured by narrowing and sharpening of the band. And position on the y-axis can be measured at any time for any pair of amplitudes whose energy gap corresponds to that band, by how narrow or broad it is. We can follow position on the y-axis for all pairs of amplitudes of a one or a system of coupled quantum degrees of freedom on a quantum graph, by the breadth of such bands. In addition, coherence can be measured using spin echo experiments.

Our first results modeled decoherence with a Wiener process, σWdt, whose variance sigma could be altered from 0, hence persistently quantum coherent in the absence of any decoherence, to infinite, which randomizes all phases. Thus, in general, as we move by increasing sigma in the Weiner process, we move from quantum to decoherence to classical behavior. For a kicked quantum rotor, position on the x-axis (degree of order) is determined by the intensity of momentum kicks, of intensity K, to the quantum rotor. These kicks are Dirac delta functions—that is "instantaneous" inputs of momentum energy supplied, without loss of generality, by laser light of any diversity of frequencies, and at any rate of photon kicks, i.e., intensity K, to the quantum rotor per unit time.

It will be clear to those of ordinary skill in the art, that the photon kicks can be any quantum degree of freedom and delivered with any time constant or varying modulated intensity, hence the kicks to each quantum degree of freedom are a quantum time modulated input signal to the quantum degree of freedom. Therefore, in general, this quantum input constitutes quantum information received by the rotor. When we generalize to a quantum network with rotors coupled to one another, or more general systems with quantum and classical degrees of freedom, this will become the quantum information via one or a plurality of quantum inputs to a system of quantum and classical degrees of freedom that responds to the incoming quantum information, emits quantum information to its environment, alters its Poised Realm and classical behaviors and also the quantum and classical Hamiltonians, and constitutes a new class of embodied quantum information processing systems that we call Trans-Turing Systems. Due to the superpositions noted above or pure states and the Born rule, coupled with decoherence to classicality or quantum measurement, the Trans-Turing system is not definite, so not algorithmic, but due to the classical degrees of freedom and Poised Realm degrees of freedom, the behavior is also not random in the standard sense of quantum random given by the Schrodinger equation and von Neumann axiomatization of closed system quantum mechanics. We emphasize that our Poised Realm systems in general and Trans-Turing systems are open quantum systems, with a distinction between the quantum system and its environment into which it can lose phase information.

Decoherence happens in open quantum systems because phase, and also amplitude, information is lost from a quantum system, here our single quantum degree of freedom, to a quantum "environment". For example a photon emitted by an excited electron may, on one of its many possible paths in Feynman sum over histories formulation of quantum mechanics and quantum electro-dynamics, interact with any quantum degree of freedom in the environment and thereby induce decoherence.

In our studies of the driven quantum rotor, we model two processes. We model the kicks, K, which hit the rotor once per arbitrary period. As noted above, we model the decoherence process as a random walk called a Weiner process, described by σW dt. W is a Gaussian distributed 0 mean, 1 variance distribution of "step sizes" which describes the phase change of the point on the circle in the complex plane at each application of the Weiner random walk, during dt. At sigma=0, there is no alteration of phase, hence no decoherence, and the system is fully quantum. Thus, σW dt=0 is the quantum coherent origin of the y-axis. As σ increases to ever larger values, the phase becomes ever "noisier" driven by the white noise Weiner process. Thus as sigma increases the rate of decoherence increases.

A second way we implement quantum measurement of an amplitude in our algorithmic simulations of a Poised Realm system is by taking the square of its modulus, (i.e., the Born Rule), doing so for all amplitudes of the rotor with finite modulus, then choosing one of these amplitudes with a probability corresponding, via the Born Rule, to its squared modulus, and placing the rotor in that single eigen state corresponding to the measured amplitude.

Once the quantum degree of freedom is measured, and in its eigen state, it can leave that eigen state quadratically in time with the "flowering" to finite moduli, of nearby and more distant amplitudes in the absence of decoherence. In short, at σ=0, no decoherence, full quantum behavior reemerges with all possible amplitudes for the system. At finite sigma, a finite number of amplitudes with finite moduli will flower as noted below.

Quantum localization of chaotic dynamics. If the classical limit of the quantum system has a Hamiltonian corresponding a position on the x-axis to the right of the critical point second order phase transition, the classical system exhibits chaos. If decoherence is 0 or low enough, because sigma is low enough, quantum behavior occurs, even in the persistent presence of some decoherence, but the quantum behavior is localized. In the Poised Realm, only a finite number of amplitudes have finite moduli.

In short, in the Poised Realm FAPP only a finite and tunable number of amplitudes are present in the quantum behavior of a single quantum kicked rotor degree of freedom, or for any number of independent kicked quantum rotors. The same limited number of amplitudes obtains for kicked quantum oscillators whether single or, if independent, any number.

Energy scaling of decoherence. In our specific, non-limiting example of the use of the Weiner process to model decoherence of any amplitude, we have found that high energy amplitudes are ones most likely to decohere to classical behavior, that is they become classical degrees of freedom, even for small values of sigma. By contrast, low energy, small modulus amplitudes do not decohere to classical behavior as readily.

The preferential decoherence of high energy and high amplitude modes is reminiscent of Fermi's Golden Rule for quantum measurement for coherent systems, where quantum systems tend to take the largest energy drop, eg to the ground state, available. But in turn, as exemplified by the famous photoelectric effect where absorption of a photon, according to Einstein 1905, kicks out an electron from the material, the transfer of energy from the quantum amplitude to the now classical degree of freedom will be largest if high amplitude high energy amplitudes preferentially decohere to classicality fapp, or are preferentially measured in the poised realm following fermi's golden rule. This bears on essential three topics: i, the efficiency of energy transfer in the Poised Realm and Trans-Turing systems; ii. The use we make below of this preferential decoherence of high energy amplitudes to solve the famous frame problem in algorithmic computers in our non-algorithmic, non-deterministic, but non-random Trans-Turing systems—see below. iii. We will use the preferential decoherence to classicality FAPP or via measurement, below in Trans-Turing systems such that there is an ongoing decoherence of high amplitude modes to classical behavior, thereby altering the classical hamiltonian, eg as a non-limiting example by altering the couplings among classical degrees of freedom. In turn this will alter the hamiltonian of the quantum degrees of freedom, in turn altering via constructive and destructive interference of superpositions, or of pure states, which amplitudes are of high energy and decohere next in time, again altering the classical and quantum hamiltonians of the trans-turing system. In turn, by recoherence, classical degrees of freedom can recohere, again altering the classical and quantum hamiltonians. This ongoing behavior is the centerpiece of trans-turing non-determinate, non-algorithmic, yet non-random behavior.

With respect to preferential deocherence of high energy amplitudes, we reason that high energy amplitudes have high angular momentum hence are less affected by random decoherence noise, so we have scaled, as a non limiting computational study example, decoherence via the Weiner process to decrease either exponentially or as a power law, with increasing energy of the amplitude. In particular, we use $\sigma = \sigma_0 \exp(E/Eo)$ where $\sigma_0$ is the sigma for a 0 energy amplitude, a constant, E is the energy of an amplitude, and Eo is a scaling factor governing the exponential fall off of Weiner modeled phase decoherence with the energy, E, of an amplitude.

Quantum Reservoir Computer

One embodiment utilizing a system operating in the poised realm is quantum reservoir computer, which is an embodied quantum variation of a classical reservoir computer known in the art. In this embodiment, the nodes within the reservoir are physical entities having at least one quantum degree of freedom that is capable of coupling (e.g., via superposition of states) to quantum degrees of freedom in other nodes in the reservoir. Unlike current quantum computers that utilize qubits, a quantum reservoir computer does not require that all elements (i.e., nodes) in the reservoir be fully quantum coherent. Rather, the quantum parallelism in the system is exploited in a self-organizing manner. Thus, the system can, in some embodiments, operate at room temperature.

The reservoir of the quantum reservoir computer can be viewed as a collection of weakly interacting discrete quantum degrees of freedom. The reservoir may comprise any fixed number of physical entities (referred to herein as "nodes") having at least one quantum degree of freedom. In one embodiment, the nodes are chromophores, which may including a biological chromophore such as a photosynthetic unit (e.g., chlorophyll, with or without it's accompanying antenna proteins), a non-biological organic chromophore (e.g., highly conjugated organic compounds), or an inorganic chromophore such as an inorganic metal complex. In one embodiment, chromophores are selected having a relatively long, but finite, coherence lifetime (e.g., as is found in chlorophyll).

In another embodiment, the nodes in the reservoir are spins or magnetic moments. Any known spin or magnetic systems may be used, including for example paramagnetic or ferromagnetic compounds or nanostructures. In one embodiment, an artificial spin system such as is the commercially available in the D-WAVE system may be used, which utilizes superconducting current to simulate spins.

In some embodiments, the quantum reservoir can be tuned to achieve a desired coherence time. For example, decoherence may be added by applying a random noise potential. The system may be tuned into the desired Poised-realm state by adjusting this potential. This way, a quantum reservoir is realized that is not fully coherent, but has a very long coherence time. Repeated measurements of this system reset its quantum coherence, which decays very slowly. Thus, this system can be kept coherent for a sufficiently long time, so that superposition states stay alive for the time intervals of single calculation steps.

The quantum degrees of freedom utilized in the reservoir may be any degree of freedom that may be coupled between the nodes as well as coupled to an input and output signal. Non-limiting examples of quantum degrees of freedom include electronic excitation states, quantum spin (e.g., electron spin and nuclear spin), quantum angular momentum, and quantum linear momentum.

Figure 4:
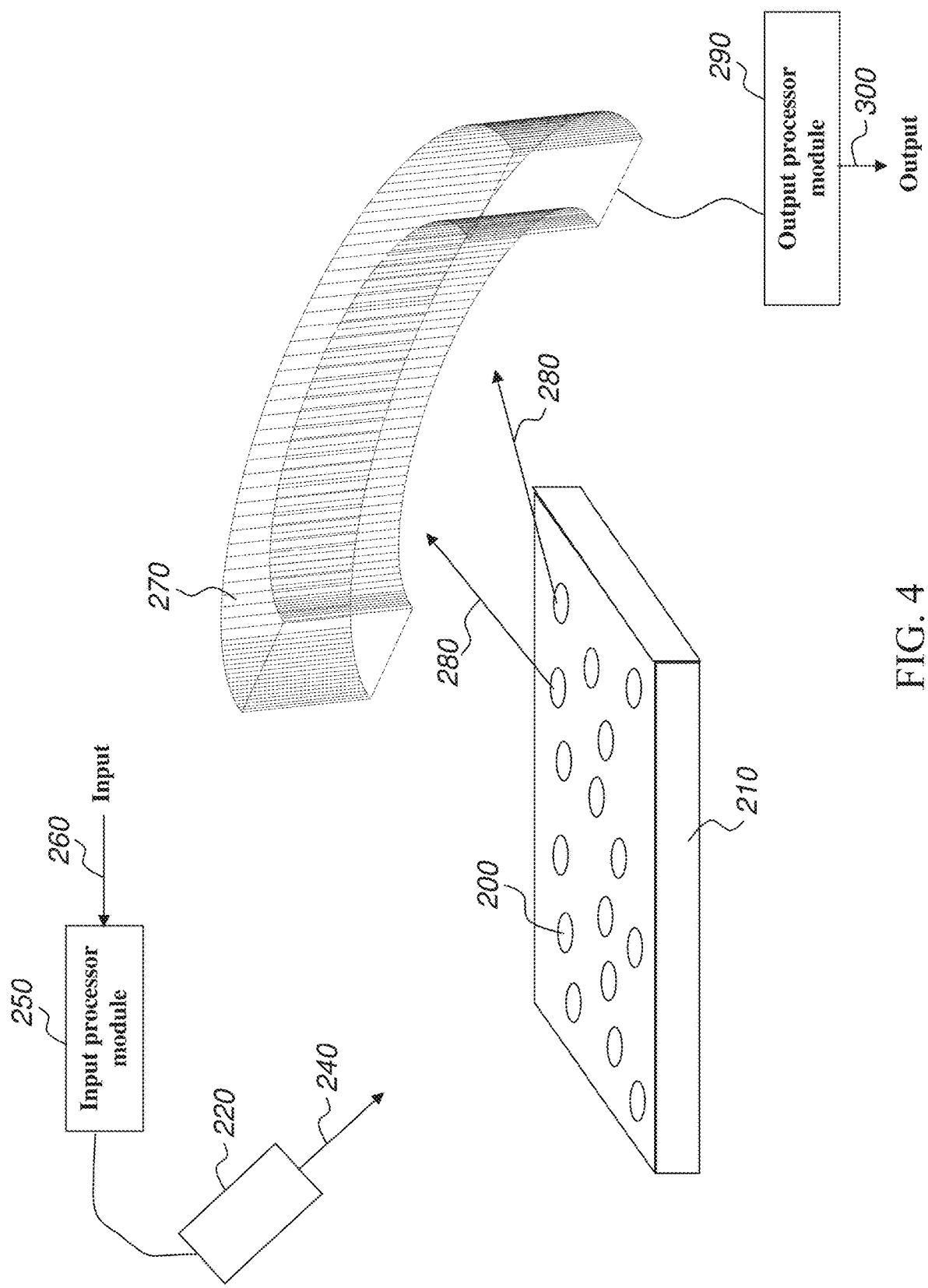
FIG. 4 is a block diagram of a computer utilizing quantum nodes and time-varying inputs and outputs.

With reference to FIG. 4, a plurality of nodes 200 are contained within or on a substrate 210. In some embodiments, the nodes 200 are fixed in or on the substrate. For example, a glass, silicon, or mica wafer may be used as a substrate 210 and the nodes 200 are adsorbed or deposited onto the surface of the substrate 210. In other embodiments, the nodes 200 are free to move within the substrate 210. For example, in some embodiments, the substrate 210 may include a liquid medium within which the nodes 200 are dispersed or dissolved. In some embodiments, the nodes 200 are distributed in a regular array (such as by using established microfabrication techniques). In other embodiments, the nodes 200 are randomly distributed.

In one non-limiting example, the nodes 200 are photosynthetic units that are deposited on a mica substrate using adsorption from solution. One such technique is described in Scheuring et al., *The EMBO Journal* (2004) 23:4127-4133, which is incorporated herein by reference in its entirety. In this technique, cell membranes containing photosynthetic units from *Rhodospirillum photometricum* are dissolved into dodecylmaltoside solution. The resulting extract is placed on freshly cleaved mica using an adsorption buffer drop. The resulting structure includes a plurality of photosynthetic units distributed across the surface of the mica.

The quantum reservoir described above may be used to build a non-algorithmic computational architecture based on the principles of neural networks, such as echo state networks or liquid state machines. The general idea is (i) to drive a random, large, fixed quantum recurrent neural network with an input signal, thereby inducing in each node within the reservoir to produce a nonlinear response signal, and (ii) produce a desired output signal by a trainable linear combination of all of these response signals.

In some embodiments, the input signals comprise a quantum driving force that couple to one or more quantum degrees of freedom of the nodes 200. Non-limiting examples of suitable input signals include photons, electrons, and electrical or magnetic fields. In one embodiment, the input signal is supplied to all nodes 200. For example, with reference to FIG. 4, a laser 220 may send laser pulses 240 of appropriate frequency to couple to a quantum degree of freedom in the nodes 200.

To translate a real-world classical input to the quantum mechanical input signal 240, an input processor module 250 may be provided. This module comprises a traditional algorithmic computer, such as a general purpose computer, that receives a classical input signal 260 and drives the input signal generator (e.g., laser 220) based on the classical input signal 260. For example, a time-varying analog electrical signal may be provided to the input processor module 250, which then translates that signal into appropriate time-varying driving of the signal generator 220. Thus, a time-varying classical input 260 results in a time-varying quantum input signal 240 being supplied to the nodes 200. For example, time-varying current or voltage may be provided to the input processor module 250, which then drives laser 220 to produce a corresponding time-varying change in pulse frequency, light frequency, or intensity of laser light 240 being supplied to the nodes 200.

In response to the quantum stimulation and the quantum coupling of the nodes 200 to each other, nodes 200 may radiate out a quantum response signal, such as scattered photons. Each node 200 can radiate an output signal and that signal may radiate in multiple directions. Some embodiments provide a detector 270 that detects the time-varying output signals 280. In the case of scattered photons, the output signals may be detected using photodetectors or a spectrometer. In some embodiments, the detector 270 includes an array of subdetectors in order to detect output signals 280 emitted in different directions. Other suitable detectors may include a nuclear magnetic resonance detector or an electron paramagnetic detector.

The result of the detection described above is a plurality of time-varying output signals. The multiplicity of the signals may be provided by detecting the time variation of a variety of parameters, such as the time variation of a plurality of frequencies of scattered photons or the time variation of photons scattered in a plurality of directions. The plurality of output signals may then be relayed to an output processor module 290. The output processor module 290 applies weights or other signal processing algorithms to the plurality of output signals to produce a single output signal 300. This module comprises a traditional algorithmic computer, such as a general purpose computer, that receives the plurality of output signals from the detector 270 and calculates the output signal 300.

Figure 5:
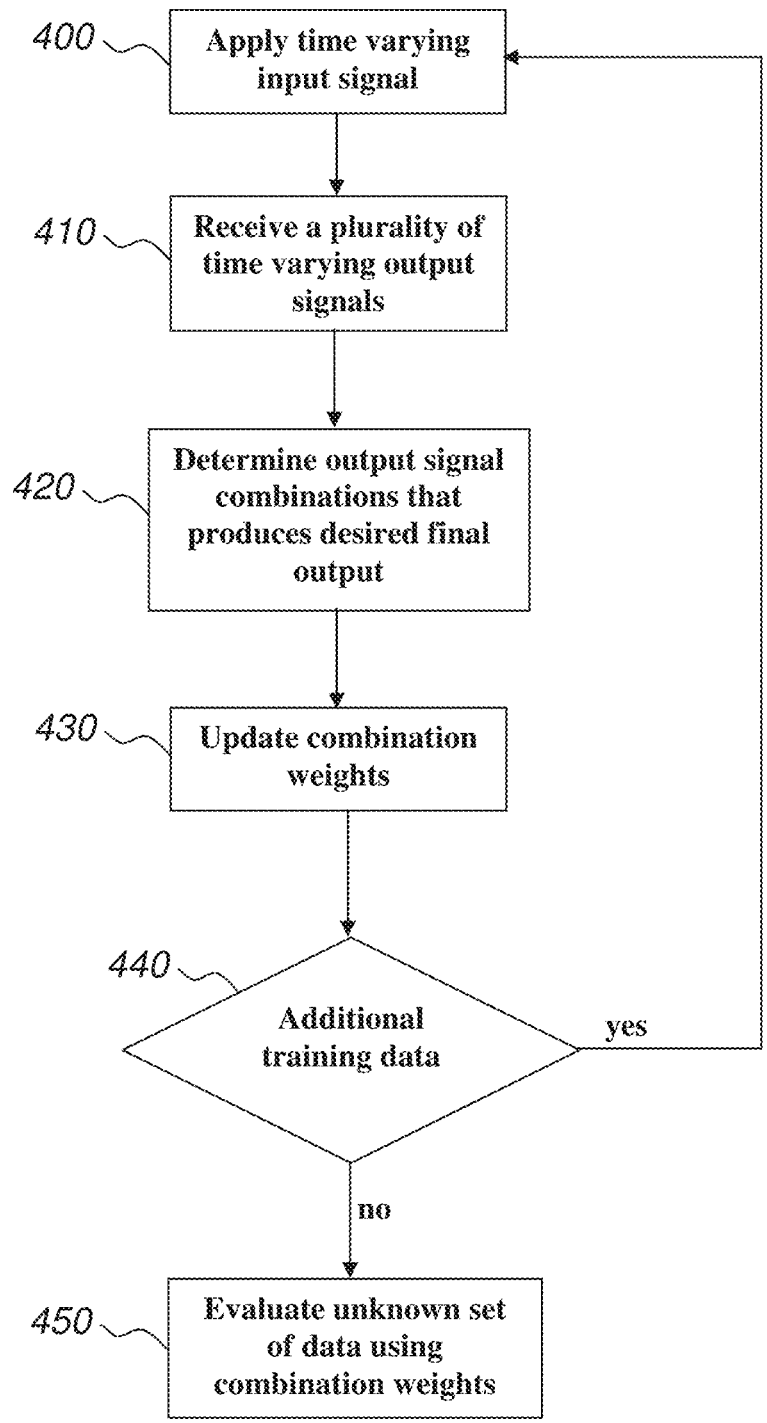
FIG. 5 is flowchart illustrating a training method for the computer described in FIG. 4.

The weights or other signal processing algorithm used to derive the output signal 300 from the plurality of outputs 280 produced by the nodes 200 may be determined using one or more training procedures, such as is known in classical reservoir computing. One example of such a training method is depicted by the flowchart in FIG. 5. At block 400, a time-varying input signal for which there is a known, desired output is provided to the quantum reservoir as discussed above. At block 410, a plurality of time-varying output signals is received by a detector as discussed above. These signals as well as the desired final output are sent to the output processor module. The output processor module determines a weighted combination or a set of weighted combinations of the plurality of output signals that will produce the desired final output. In one embodiment, the weighted combination of outputs is a linear combination. In other embodiments, more complicated functional forms are utilized. In some embodiments, the output processor module determines the optimal functional form. Once a suitable combination is determined that produces the desired output, the corresponding weights are stored in memory.

At block 440, it is determined whether there is any additional training data (i.e., another known input-output combination). If so, the procedure returns to block 400 for input of the additional data. When block 420 is reached, the appropriate combination weights are determined that produces the desired output that is also consistent with all previous training data. The new weights are updated into memory at block 440. If no more training data is supplied, the procedure proceeds to block 450, where a set of input data having no known output is supplied to the quantum reservoir. The stored combination weights are applied to the plurality of output signals in order to produce the final output.

In one non-limiting example, the above described quantum reservoir computer may be implemented using a simulated spin system, such as provided by D-WAVE. The commercially available D-WAVE computer contains a plurality of qubits consisting of superconducting currents that simulate spin. The inputs and outputs are electrical current. In its intended mode of operation, the D-WAVE computer operates using only fully quantum coherent qubits and non-time-varying input (i.e., a traditional quantum computer approach). However, in the present context, all simulated spins, including those that are not fully quantum coherent are used as nodes for the quantum reservoir. Furthermore, a time-varying input signal and plurality of output signals is provided. With a proper $J_{ij}$ and $h_i$ set, the D-Wave Hamiltonian:

$$Hp = \sum_{i=1}^{N} h_i \sigma_i^z + \sum_{i,j} J_{ij} \sigma_i^z \sigma_j^z,$$

can be guided through a finite size version of the metal-insulator transition. At various low temperatures, the interplay of thermal decoherence and the spectrum can be determined to achieve the properties necessary for use as a quantum reservoir.

Hybrid Quantum-Classical Computing System

Another embodiment of a computing system operating in a regime that is neither fully quantum nor fully classical utilizes a plurality of quantum processors that are coupled by classical means to form large hybrid quantum-classical architectures that can solve problems approximately, involving more qubits than a single fully quantum processor. In some embodiments, the hybrid system includes a plurality of independent quantum processors where each quantum processor comprises a plurality of entangled qubits. When in operation, the mean value of the qubits in each independent quantum processor is measured and used to construct signals that are applied to the qubits in each other quantum processor. In other words, each qubit is modulated by the mean values of qubits in all other quantum processors in the system.

Figure 6:
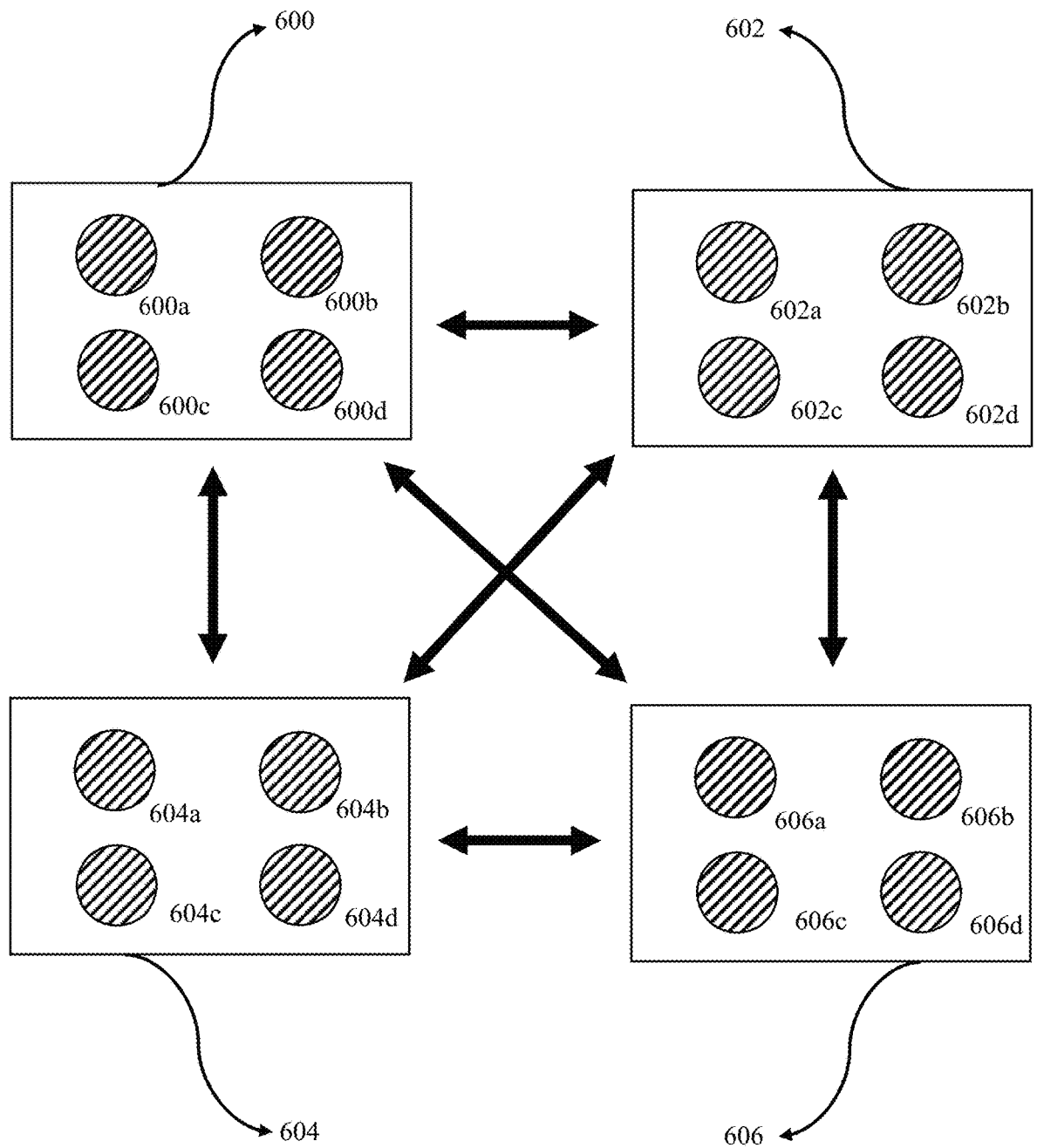
FIG. 6 is a block diagram of a hybrid quantum-classical computing system.

The basic architecture is illustrated in FIG. 6 in one non-limiting example. A plurality of quantum processors 600, 602, 604, and 606 are provided. Each quantum processor comprises a plurality of qubits. Processor 600 comprises qubits 600a, 600b, 600c, and 600d. Processor 602 comprises qubits 602a, 602b, 602c, and 602d. Processor 604 comprises qubits 604a, 604b, 604c, and 604d. Processor 606 comprises qubits 606a, 606b, 606c, and 606d. The qubits within each quantum processor are entangled with each other, but are not entangled with the qubits in any other processor. During operation, the mean values of qubits in each quantum processor are read. Signals are constructed by combination of these values, which are then applied to the qubits in each other quantum processor. Thus, for example, a signal is applied to the qubits in processor 602 that is constructed by a combination of the mean values of the qubits in each of processors 600, 604, and 606. This process applies across all quantum processors such that the signals applied to the qubits in a given quantum processor are based on a combination of the mean values of the qubits in each other quantum processor. The combination of the mean values used to construct the various signals may be a weighted linear or non-linear combination of the values depending on the final Hamiltonian whose solution is desired.

In various embodiments, each quantum processor comprises a number of entangled qubits independently selected from 2, 3, 4, 5, 6, 7, 8, 9, 10, or more qubits. In various embodiments, the number of entangled qubits in each quantum processor is from 2 to 5000, 2 to 2000, or 2 to 1000, from 2 to 500, from 2 to 250, from 2 to 100, from 2 to 100, from 2 to 10, or from 2 to 8. In various embodiments, the number of quantum processors utilized are 2, 3, 4, 5, 6, 7, 8, 9, 10, or more. In various embodiments, the number of quantum processors utilized range from 2 to 100, 2 to 50, 2 to 25, 2 to 10, or 2 to 5.

Figure 7:
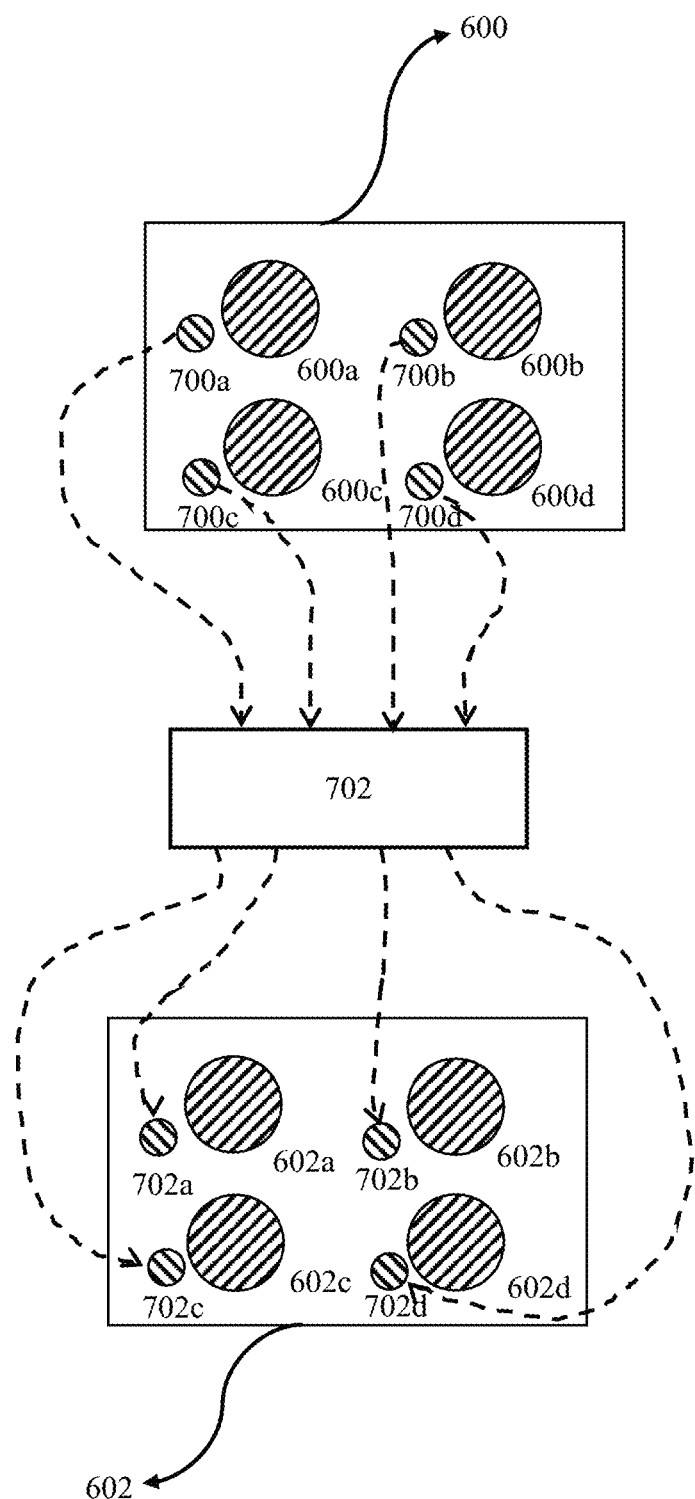
FIG. 7 is a block diagram illustrating connection between distinct quantum processors.

The architecture is illustrated in more detail in FIG. 7, focusing on two of the quantum processors, 600 and 602. Quantum processor 600 includes detection elements 700a, 700b, 700c, and 700d associated with each qubit 600a, 600b, 600c, and 600d. The detection elements 700a, 700b, 700c, and 700d are configured to measure the state of each qubit 600a, 600b, 600c, and 600d. Signals from each detection element 700a, 700b, 700c, and 700d are fed into classical processor electronics 702, which may be any high frequency analog and/or digital electronics suitable for processing the signals. Processor electronics 702 generates new signals based on the inputs from the detections elements 700a, 700b, 700c, and 700d. This new signals may be, for example, weighted linear or non-linear combinations of the values measured by the detection elements. These new signals are then applied to signal transmission elements 702a, 702b, 702c, and 702d, which are associated with each qubit 602a, 602b, 602c, and 602d in processor 602. The signal transmission elements 702a, 702b, 702c, and 702d then couple the signas to each of qubits 602a, 602b, 602c, and 602d. As discussed above with respect to FIG. 6, the system illustrated in FIG. 7 will also read the states of qubits 602a, 602b, 602c, and 602d in processor 602 and use those values to generate signals applied to the qubits 600a, 600b, 600c, and 600d in processor 600. Similarly, states of qubits in other quantum processors in the system will also be read and used in constructing the signals applied to the qubits in processors 600 and 602. In some embodiments, the detection elements 700a, 700b, 700c, and 700d may also be used as signal transmission elements for purposes of coupling a signal to qubits 600a, 600b, 600c, and 600d, and signal transmission elements 702a, 702b, 702c, and 702d may also be used as detection elements for detecting the states of qubits 602a, 602b, 602c, and 602d.

In the system described above, any suitable qubit architecture may be used, including qubits based on macroscopic quantum phenomena, such as superconducting quantum devices and laser based optical qubits. For example, superconducting qubits may be used, where the quantum state of the superconducting qubit is a charge quanta, a magnetic flux quanta, a quantum charge oscillation, or a combination thereof. In one non-limiting example, the qubit is an ac SQUID element, where the quantum state is the magnetic flux through the ac SQUID. In such a qubit, the state of the qubit may be read by measuring the current through the ac SQUID. The current may be a nonlinear monotonous function of the mean value of the qubit. Thus, in some embodiments, the system is calibrated to correlate the current with the mean value of the qubit. The current may be read by any suitable means, including a dc SQUID element that is positioned adjacent to each ac SQUID element. In some embodiments, the procedure described by [Berkeley et al., 2010] (incorporated herein by reference in its entirety) may be used, which positions a quantum flux parametron and dc SQUID adjacent to each ac SQUID. These elements may then be used to read the mean values of each qubit in order to construct a signal based on these values and apply the signal to qubits in other quantum processors, which may also have the same architecture. The elements may also be used to apply the constructed signals to qubits, for example, in inductive coupling to the ac SQUID.

In another non-limiting example, laser based optical qubits are used, such as those described in [Inagaki et al, 2016] and [McMahon et al., 2016] (both of which are incorporated herein by reference in their entirety). In these systems, the qubit is created using a measurement and feedback system utilizing high-frequency electronics such as a field-programmable gate array (FPGA). The state of the qubit is encoded in a degenerate optical parametric oscillator phase. The detection element of this phase may include a beam splitter to couple out a small fraction of the optical beam and then measure the phase using a homodyne detector. The mean values measured from each qubit is then used to construct modulation signals using the FPGAs in the qubits of the other quantum processors. In other words, the standard feedback signal is modulated by the values measured for qubits in other quantum processors.

Any other qubit, detection elements, and signal transmission elements known in the art may be used for the system described above. Further non-limiting examples of qubit architectures include trapped-ion quantum computers, which include ions, or charged atomic particles, confined and suspended in free space using electromagnetic fields. Qubits are stored in stable electronic states of each ion. Coupling of such states may be achieved using lasers. Another example includes a nuclear magnetic resonance quantum computer utilizing spin states of nuclei as qubits. Quantum states in such a system may be probed and affected using standard nuclear magnetic resonance techniques.

Figure 8:
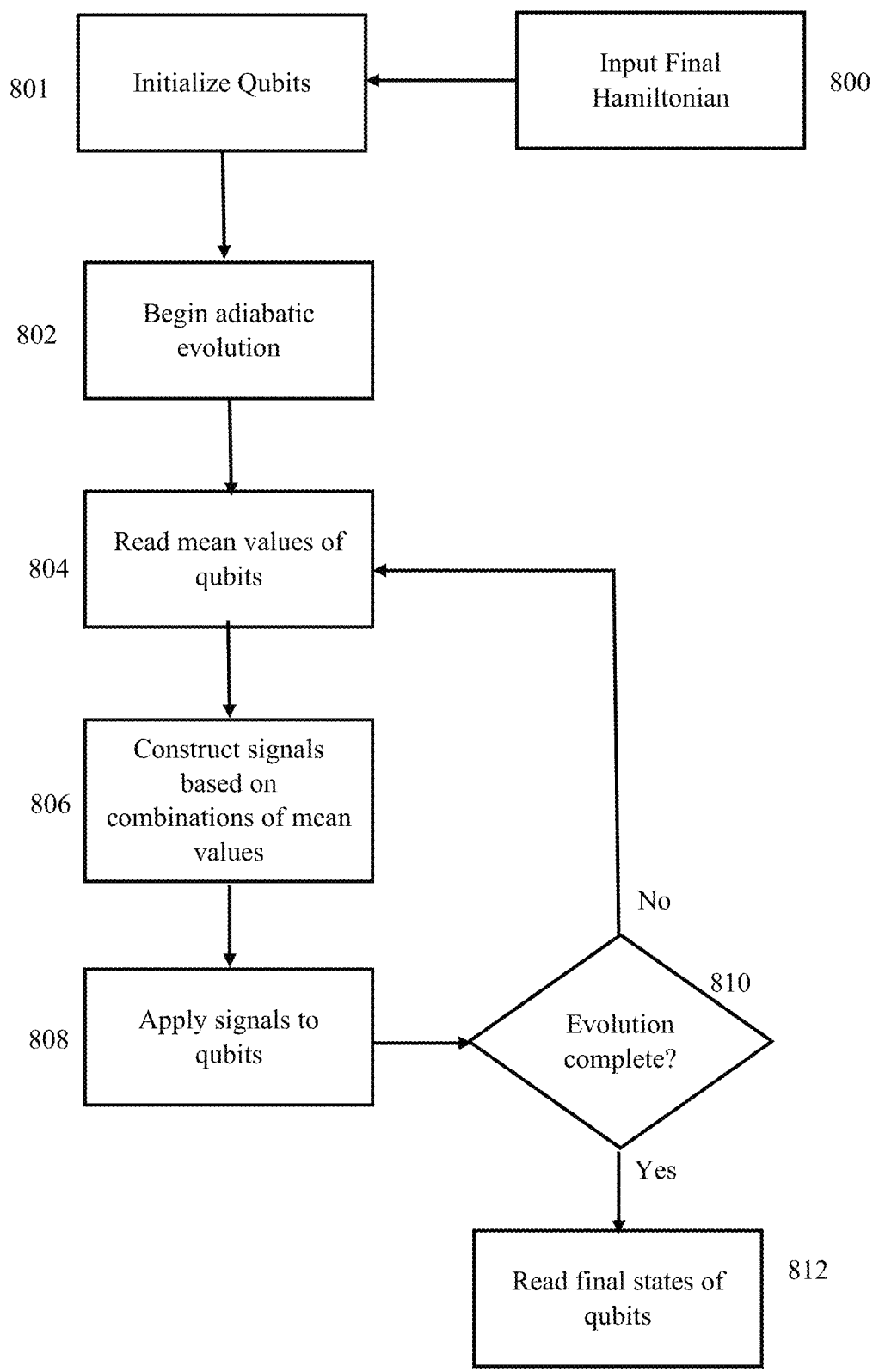
FIG. 8 is a flow chart illustrating a process for using a hybrid quantum-classical computing system.

With reference to FIG. 8, the above-described system may operate as follows. At step 800, the final Hamiltonian whose eigenvalue solution is desired is input into the system. For example, in the Ising Hamiltonian having the form:

$$H_{fin} = \sum_i h_i \sigma_i^z + \sum_{ij} J_{ij} \sigma_i^z \sigma_j^z,$$

the interaction values $J_{ij}$ may be input into the system. In this case, the Hamiltonian assumes that all qubits in the system are part of the same entangled quantum processor even though, as described above, the qubits are actually divided into separate entangled sets of qubits. At step 801, the qubits in all quantum processors are initialized into a desired state based on an initial Hamiltonian. At step 802, each quantum processor is evolved adiabatically toward the final Hamiltonian using techniques known in the art depending on the qubit architecture used. During this evolution, the mean value of all qubits is measured using the detection elements at step 804. At step 806, these values are used to construct signals to be applied to the various qubits in the system. For example, signals may be constructed for each qubit in a quantum processor that is a weighted linear or non-linear combination of the mean values of qubits measured for each other quantum processor. In some embodiments, the signal for qubit i in one quantum processor is a weighted linear combination of the values read for all qubits j in the other quantum processors, where the weights are the interaction values $J_{ij}$ between the qubits in the desired final Hamiltonian. In other words, the signal applied to qubit i has the form:

$$\tilde{h}_i(t) = h_i + \sum_{j \in A_i} J_{ij} \langle \sigma_j^z \rangle,$$

At step 808, the respective signals are applied to each qubit in the system. At decision step 810, it is determined whether adiabatic evolution is complete. If not, the system continues to read mean qubit values, construct modulation signals based on those values, and apply those signals to the various qubits continuously during the adiabatic evolution. If evolution is complete, the final states of the qubits are read at step 812 and fed to a classical processor for output or further processing.

The theory of operation of the above-described system is based on using the variational method to find the minimum of the functional $$\varepsilon_0(s) = \frac{\langle \Psi(s) | \hat{H}_{tr}(s) | \Psi(s) \rangle}{\langle \Psi(s) | \Psi(s) \rangle},$$

where the variational wave function $\Psi$ is restricted to some part of the Hilbert space. We consider here product wave functions, which are generalizations of the Hartree product form (7). We can group our quantum degrees of freedom into $k = 1, \ldots, \Omega \leq N$ disjoint sets $A_k$ so that each degree belongs only to one of them. The degrees are indexed as $q_i^k$, where $i = 1, \ldots, N_k$ and $N_k$ is the number of degrees in set $A_k$. Then the product form variational wave function is $$\Psi = \prod_{k=1}^{\Omega} \psi_k(q_i^k). \tag{11}$$

The product consists of wave functions $\psi_k(q_i^k)$, which depend on quantum variables belonging to the set $A_k$ only. The physical meaning of this choice is that quantum degrees in the same set are entangled, while degrees belonging to different groups are not. For the s=0 initial Hamiltonian and for the s=1 final Hamiltonian the exact ground state of the transitional Hamiltonian is a product wave function (11) and the variational minimum coincides with the exact ground state so that $\varepsilon_0(0) = E_0(0)$ and $\varepsilon_0(1) = E_0(1)$. We then can start at s=0 from the known ground state of the initial Hamiltonian and can change s adiabatically. During the adiabatic time evolution we stay in the variational ground state, the lowest energy state permitted by the restricted form of the variational wave function. The time evolution of a variational wave function $\Psi(t)$, which for time t minimizes the variational functional $$\frac{\langle \Psi(t) | \hat{H}(t) | \Psi(t) \rangle}{\langle \Psi(t) | \Psi(t) \rangle}$$

is given by the generalized Dirac-Frenkel-McLachlan (GDFM) equation. Instead of solving the time dependent Schrödinger equation adiabatically we have to solve the GDFM equation (9) generalized for the product wave function (11). At the end of the adiabatic evolution we get to the variational ground state of the final Hamiltonian. This way, we can find the ground state of the desired Hamiltonian without relying on fully coherent quantum evolution.

We give here the generalized Dirac-Frenkel-McLachlan (GDFM) time-dependent self-consistent equation. We group the variables of the Hamiltonian (8) according to the sets $A_k$ so that $$\hat{H}(t) = \sum_{k=1}^{\Omega} \hat{H}_k(q_i^k, t) + \sum_{k<l} \hat{V}_{kl}(q_i^k, q_j^l, t), \tag{12}$$

where $\hat{H}_k$ contains variables from set $A_k$ and $\hat{V}_{kl}$ from $A_k$ and $A_l$ only. Then we can write the GDFM equations as $$i\hbar \partial_t \psi_k(q_i^k, t) = (\hat{H}_k + \hat{G}_k)\psi_k(q_i^k, t), \tag{13}$$

where $$\hat{G}_k(q_i^k, t) = \sum_{l \neq k} \int \psi_l^*(q_j^l, t) \hat{V}_{kl}(q_i^k, q_j^l, t) \psi_l(q_j^l, t) dq_j^l, \tag{14}$$

is the interaction averaged over the wave functions corresponding to the other $l \neq k$ wave functions $\psi_l(q_j^l, t)$.

In existing real world realizations the Hamiltonians (4) and (5) are used. The Generalized Dirac-Frenkel-McLachlan time-dependent self-consistent equations can be developed for this case as well. The variational wave function can be written in the form $$\Psi(t) = \prod_{k=1}^{\Omega} \psi_k(S_i^k, t), \tag{15}$$

where $S_i^k = \pm 1$ and i is the index of the qubit belonging to set $A_k$. The wave functions can be expanded in the basis of the qubits in set $A_k$ $$\psi_k = \sum_{S_i^k = \pm 1} C_k(S_1^k S_2^k, \ldots S_{N_k}^k, t) \left| S_1^k S_2^k \ldots S_{N_k}^k \right\rangle. \tag{16}$$

The transitional Hamiltonian can be written as $$\hat{H}(s) = \sum_k \hat{H}_k(s) + \sum_{k<l} \hat{V}_{kl}(s),$$

where we separate terms corresponding to qubits belonging to set $A_k$ $$\hat{H}_k(s) = -(1-s)\Delta \sum_{i \in A_k} \sigma_i^x + s \sum_{i \in A_k} h_i \sigma_i^z + s \sum_{i<j \in A_k} J_{ij} \sigma_i^z \sigma_j^z,$$

and the terms describing the interactions of qubits belonging to different sets $A_k$ and $A_l$ $$\hat{V}_{kl}(s) = s \sum_{i \in A_k, j \in A_l} J_{ij} \sigma_i^z \sigma_j^z.$$

The averaged operator becomes $$G_k(s) = s \sum_{i \in A_k, j \in A_l} J_{ij} \sigma_i^z \langle \sigma_j^z \rangle,$$

where the average is for the wave function corresponding to set $A_l$ $$\langle \sigma_j^z \rangle = \sum_{S_i^l = \pm 1} S_j^l \left| C_l(S_1^l S_2^l, \ldots S_{N_l}^l, t) \right|^2.$$

Finally, the self-consistent Hamiltonian is $$\hat{H}_k + \hat{G}_k = -(1-s)\Delta \sum_{i \in A_k} \sigma_i^x + s \sum_{i \in A_k} \tilde{h}_i(t) \sigma_i^z + s \sum_{i<j \in A_k} J_{ij} \sigma_i^z \sigma_j^z, \tag{17}$$

where the effective time dependent magnetic field $$\tilde{h}_i(t) = h_i + \sum_{j \in A_l} J_{ij} \langle \sigma_j^z \rangle,$$

has been introduced. The wave function at t=0 is initialized in the ground state of the initial Hamiltonian $$C_k(S_1^k S_2^k \ldots S_{N_k}^k) = \frac{(-1)^{\sum_i (S_i^k - 1)/2}}{2^{N_k/2}}. \tag{18}$$

Then the adiabatic GDFM equation becomes $$i\hbar \dot{C}_k(S_1^k S_2^k \ldots S_{N_k}^k) = \tag{19}$$
$$\sum_{S_i^{k'} = \pm 1} \langle S_1^k S_2^k \ldots S_{N_k}^k | \hat{H}_k + \hat{G}_k | S_1^{k'} S_2^{k'} \ldots S_{N_k}^{k'} \rangle C(S_1^{k'} S_2^{k'} \ldots S_{N_k}^{k'}),$$

where the $2^{N_k} \times 2^{N_k}$ Hamiltonian matrix is given by the matrix elements calculated between qubit eigenstates $$\langle S_1^k S_2^k \ldots S_{N_k}^k | \hat{H}_k + \hat{G}_k | S_1^{k'} S_2^{k'} \ldots S_{N_k}^{k'} \rangle =$$
$$\sum_{i=1}^{N_k} -\frac{1-s}{2} \Delta (1 - S_i^k S_i^{k'}) + \frac{s}{2} \tilde{h}_i(t)(S_i^k + S_i^{k'}) + \sum_{i<j} \frac{s}{4} J_{ij}(S_i^k + S_i^{k'})(S_j^k + S_j^{k'}).$$

The total number of differential equations (19) to be solved is $N_T = \sum_{k=1}^{\Omega} 2^{N_k}$. Note, that for the fully quantum scheme ($\Omega=1$ and $N_1=N$) $N_T = 2^N$ differential equations of the type (19) have to be solved, which scales exponentially with the number of qubits. If the qubits are not entangled at all ($\Omega=N$ and $N_k=1$) we get a scheme, where only the average values of the qubits enter into the calculation. We can call this the Meanfield Quantum Adiabatic Annealer (MQAA) scheme. In this case the number of differential equations $N_T = N$ scales with the number of qubits linearly. In the intermediate cases between the fully quantum and the fully classical (MQAA) schemes we can consider the cases, where each quantum coherent unit consists of M qubits. If the total number of qubits in the intermediate scheme is N then N/M quantum processor is used and in each quantum processor $2^M$ equations are solved. The total number of differential equations is then $N_T = 2^M$ (N/M), which scales linearly with the total number of qubits. The choice of N and M represents a trade-off, where we can trade the quality of the solution for the number of qubits. A larger M means a solution closer to the exact quantum solution, while a larger N means that a larger computational problems can be attacked this way.

Based on the foregoing analysis, the modulation signal applied to qubit i may take the form of the linear combination $\Sigma_{j \in A_l} J_{ij} \langle \sigma_j^z \rangle$, wherein the $\langle \sigma_j^z \rangle$ (t) are the mean values of the qubits of the other quantum processors. Thus, qubit i will be subject to the effective field:

$$\tilde{h}_i(t) = h_i + \sum_{j \in A} J_{ij} \langle \sigma_j^z \rangle.$$

Emulation on a Classical Computer

The hybrid quantum-classical system described above may also be emulated on a classical computer. In this embodiment, the qubits described above are not quantum qubits, but are rather models of qubits emulated in a classical computer. The mean values of each emulated qubit (generated by computer simulation) may be used to construct a simulated field that is then applied to other emulated qubits in the fashion described above. In this case, the signals and the response by the emulated qubits are simulated.

For example, in some embodiments, each quantum processor is an emulated quantum processors using a classical computer programed with a quantum mechanical model of each quantum processor. In such a model, the applicable Schrödinger equation and wave function can be solved numerically. Adiabatic evolution of each quantum processor from an initial Hamiltonian to a final Hamiltonian is simulated by iterating the model from the initial state to the final state. Simulated approaches to this adiabatic evolution may be as described in [Pier et al, 2011] or U.S. Pat. No. 9,152,746, which are incorporated herein by reference in their entirety. During the evolution, a simulated modulation (e.g., simulated field) is applied to each qubit that is a weighted linear or non-linear combination of the values of each qubit in the other modeled quantum processors at each iteration. Thus, the formalism described above is fully modeled within a classical computer.

Validation of Approach

It can be demonstrated that, even in the fully classical case, the above formalism implemented in a classical computer can outperform existing laser-optical quantum computers. In the fully classical case, $N_k=1$ and $\Omega=N$. If we use the Hartree product form $$\psi_k = \prod_{i=1}^{N} \psi_i(S_i, t), \tag{20}$$

and $$\psi_j = C_j^+ |+\rangle + C_j^- |-\rangle, \tag{21}$$

we get the simplest computing scheme, where the qubits are not entangled. In this case only the average values of the qubits enter into the calculation and we call this the Mean-field Quantum Adiabatic Annealer (MQAA) scheme. We can introduce the expectation value of the Pauli matrix operators as $$S_j^x = \langle \psi_j | \sigma_j^x | \psi_j \rangle = C_j^{+*} C_j^- + C_j^{-*} C_j^+, \tag{22}$$

$$S_j^y = \langle \psi_j | \sigma_j^y | \psi_j \rangle = i(C_j^{-*} C_j^+ - C_j^{+*} C_j^-), \tag{23}$$

$$S_j^z = \langle \psi_j | \sigma_j^z | \psi_j \rangle = C_j^{+*} C_j^+ - C_j^{-*} C_j^-. \tag{24}$$

These satisfy the relation $$S_j^{x2} + S_j^{y2} + S_j^{z2} = 1. \tag{25}$$

The variational functional can be expressed with the expectation values $$\varepsilon[\Psi] = -(1-s)\Delta \sum_i S_i^x + sH_{fin}(S_1^z, \ldots, S_N^z). \tag{26}$$

We can minimize (26) at the constraint (25) which yields $S_j^y=0$ and $S_j^x=(1-S_j^{z2})^{1/2}$ and the variational functional takes the form $$\varepsilon[\Psi] = -(1-s)\Delta \sum_i (1-S_i^{z2})^{1/2} + sH_{fin}(S_1^z, \ldots, S_N^z). \tag{27}$$

Then in the minimum the partial derivatives of the functional should vanish $$\frac{\partial \varepsilon \Psi}{\partial S_j^z} = -(1-s)\Delta \frac{S_j^z}{(1-S_j^{z2})^{1/2}} + s\frac{\partial H_{fin}}{\partial S_j^z} = 0. \tag{28}$$

The external field acting on qubit $S_i$ is $$\bar{h}_i = \frac{\partial H_{fin}}{\partial S_i^z} = h_i + \sum_j J_{ij}^{(2)} S_j^z + \sum_{jk} J_{ijk}^{(3)} S_j^z S_k^z + \ldots \tag{29}$$

The adiabatic GDFM equation in dimensionless units for the qubits becomes $$i\frac{d}{ds}\begin{bmatrix} C_j^+(s) \\ C_j^-(s) \end{bmatrix} = T_A \begin{bmatrix} s\bar{h}_j(s) & -(1-s)\Delta \\ -(1-s)\Delta & -s\bar{h}_j(s) \end{bmatrix} \begin{bmatrix} C_j^+(s) \\ C_j^-(s) \end{bmatrix}. \tag{30}$$

For the numerical solution we can introduce the discretization $s=k/N$, $k=0, \ldots, N$, and we get the following iteration $$\begin{bmatrix} C_j^+((k+1)/N) \\ C_j^-((k+1)/N) \end{bmatrix} = \tag{31}$$

$$\exp\left[-idt\begin{bmatrix} (k/N)h_i^{ext}(k/N) & -(1-k/N)\Delta \\ -(1-k/N)\Delta & -(k/N)h_i^{ext}(k/N) \end{bmatrix}\right]\begin{bmatrix} C_j^+(k/N) \\ C_j^-(k+N) \end{bmatrix}.$$

where $dt=T_A/N$. To keep the discretization error finite the condition $T_A^2/N \ll 1$ should be met. For the numerical precision N should be large, and $T_A$ should also be large to keep it adiabatic. These conditions can be met if $1 \ll T_A \ll N^{1/2}$ and the time step $dt=T/N$ is much smaller than $N^{-1/2}$. The iteration scheme can be improved further by using an adaptive time-step. During the iteration the gap between the two eigenvalues of (30) $g_i(s)=2((sh_i^{ext}(s))^2+(1-s)^2\Delta^2)^{1/2}$ can be calculated and $g_m(s)$ the minimum of $g_i(s)$–s can be selected. The minimum gap condition (3) then dictates that the basic $dt_0$ time-step should be modified as $dt=g_m^2 \cdot dt_0$ to use smaller time steps once the spectral gap becomes smaller.

One of the standard procedures to compare the performance of various optimization schemes is to run them on standardized problems. The D-Wave adiabatic quantum computer and the Coherent Ising Machine has been tested on standardized the Max-Cut problems [Hamerly et al., 2018]. The Max-Cut problem is the partitioning of the vertices of a graph into two disjoint subsets such that the weights $W_{ij}$ of edges between the two subsets is maximized. The partition then is called a cut. Max-Cut remains NP-hard even when the input is restricted to unweighted cubic graphs [Garey et al., 1974]. We can index the vertices of a graph by $i=1, \ldots, N$. We denote by $S_i=+1$ if the vertex belongs to one of the subsets and by $S_i=-1$ if it belongs to the other. We set $J_{ij}=W_{ij}$ if vertices i and j are connected and $J_{ij}=0$ otherwise. The cut value of a partition can be calculated as $$\text{Cut} = \sum_{i<j} J_{ij}(1-S_iS_j)/2,$$

which counts the number of edges belonging to two different partitions. The cut value then can be expressed as $$\text{Cut} = \frac{1}{2}\sum_{i<j} J_{ij} - \frac{1}{2}\sum_{i<j} J_{ij}S_iS_j = \frac{W}{2} - \frac{E}{2}$$

where W is the sum of weights for all edges, and the second term is the energy of the qubit system $E=\Sigma_{i<j}J_{ij}S_iS_j$. We can maximize the cut value by minimizing the energy of the configuration. In [Helmberg and Rendl, 2000], 54 large (N=2000) random graphs called G1-G54 has been introduced for testing Max-Cut problems. In [Inagaki et al., 2016], graphs G22 and G39 has been tested with the Coherent Ising Machine. The results are compared to Simulated Annealing [Kirkpatrick et al., 1983], which is one of the state of the art classical optimum search algorithms. For comparison we run the MQAA scheme for these graphs. The minimum of the Max-Cut problem is doubly degenerated since by flipping all the qubits $S_i \rightarrow -S_i$ the energy remains unchanged. Therefore, we applied field $h_1=1$ to the first site, which breaks the degeneracy and allows the convergence of the algorithm to a nontrivial solution. At the end of the simulation the signum function sgn(x) is applied to round the variables numerically to 1. In Table 1 results for for N=10.000, $dt_0$=0.1 and using the adaptive step scheme are shown.

TABLE 1

Best Coherent Ising Machine and Simulated Annealing [Inagaki et al., 2016] Max-Cut cut values for standard graphs G22 and G39 form and [Helmberg and Rendl, 2000] and the results of our Meanfield Quantum Adiabatic Annealing for 10.000 iteration steps, adaptive scheme with $dt_0$ = 0.1 is used without post processing.

|     | CIM   | SA    | MQAA  |
| --- | ----- | ----- | ----- |
| G22 | 13313 | 13336 | 13331 |
| G39 | 2361  | 2384  | 2344  |

REFERENCES—ALL OF WHICH ARE INCORPORATED HEREIN BY REFERENCE IN THEIR ENTIRETY

1. Frankenberg, N., Hager-Braun, C., Teiler, U. Fuhrmann, M., Rogl, H., Schneebauer, N., Nelson, N., and Hauska, G. (2008). P840-Reaction Centers from Chlorobium tepidum-Quinone Analysis and Functional Reconstitution into Lipid Vesicles. Photochemistry and Photobiology, 64:(1), 1-14.
2. Jones, M. R., McEwan, A. G., and jackson, J. B. (2010). The role of c-type cytochromes in the photosynthetic electron transport pathway of *Rhodobacter capsulatus*. Biochimica et Biophysica Acta—Bioenergetics, Vol 1019, issue 1, 59-66.
3. Gabellini, N. Gao, Z., Oesterhelt, D., Venturolli, G., and Melandri, B. A. (1989). Reconstitution of cyclic electron transport and photophosphorylation by incorporation of the reaction center, bc1 complex and ATP synthase from *Rhodobacter capsulatus* into ubiquinone-10/phospholipid vesicles. Biochimica et Biophsica Acta—Bioenergetics, Vol 974, issue 2: 202-210.
4. Varga, A. R., and Staehelin, L. A. (1985). Pigment-Protein Complexes from *Rhodopsuedomas palustris*: Isolation, Characterization, and Reconstitution into Liposomes. Journal of Bactriology, vol 161 no 3: P 921-927.
5. Scholes, G. D., (2010). Quantum-Coherent Energy Transfer: Did Nature Think Of It First? The Journal of Physical Chemistry Letters, 1: 2-8.
6. Pascher, T., Polyutov, S. Yartsev, A., Pullerits, T., Lenngren, N. (2011), Photon echo spectroscopy, Wikipedia.
7. Hahn, E. L. (1950). "Spin Echoes". Phys. Rev. 80: 580-594.
8. Mezel, F. (ed) (1980) Neutron Spin Echo, Lecture Notes in Physics, vol 128, Springer
9. Science News Nov. 20, 2010. Inducing Entanglement.
10. Francis Crick, The Astonishing Hypothesis: The Scientific Search For the Soul, TOUCHSTONE, Simon an Schuster, N.Y. 1994.
11. Kauffman, S. A. Origins of Order, Oxford University Press, N.Y. (1993).
12. Kauffman, S. A. Investigations, Oxford University Press, N.Y. (2000).
13. Kauffman, S. A. Reinventing the Sacred. Basic Books, N.Y. (2008).
14. Kauffman S. A. (1986). Autocatalytic Sets of Proteins. J. Theor. Bio. 119: 1-24.
15. N. Wagner and Ashkenasy, G. (2009). Symmetry and order in systems chemistry. The Journal of Chemical Physics, 130: 164907-164911.
16. Kauffman, S. A. Origins of Order, Oxford University Press. N.Y. (1993).
17. P. L Luisi, Stano, P., Rasi, S., and Mavelli, F. (2004). A possible route to prebiotic vesicle reproduction, Artifical Life, 10: 297-308.
18. C. Fernando, Vasas, V., Santos, M., Kauffman, S., and Szathmary, E. (2011). Spontaneous Formation and Evolution of Autocatalytic Sets within Compartments. Submitted.
19. A. Filsetti, Serra, R., Carletti, T., Villiani, M., and Poli., I. (2010). Non-linear protocell models: synchronization and chaos. Eur. J. Phys. J. B 77: 249-256.
20. R. L. Hotz. (2010). Scientists Create Synthetic Organism. Wall Street Journal May 21.
21. Nykter, M., Price, N. D., Aldana, M., Ramsey, S. A., Kauffman, S. A., Hood, L., Yli-Harja, O. and Shmulevich, I. (2008). Gene Expression Dynamics in the Macrophage Exhibit Criticality. *Proc Natl Acad Sci USA* 105(6).: 1897-1900.
[Aharonov et al., 2008] Aharonov, D., Van Dam, W., Kempe, J., Landau, Z., Lloyd, S., and Regev, O. (2008). Adiabatic quantum computation is equivalent to standard quantum computation. *SIAM review*, 50(4):755-787.
[Berkley et al., 2010] Berkley, A., Johnson, M., Bunyk, P., Harris, R., Johansson, J., Lanting, T., Ladizinsky, E., Tolkacheva, E., Amin, M., and Rose, G. (2010). A scalable readout system for a superconducting adiabatic quantum optimization system. *Superconductor Science and Technology*, 23(10):105014.
[Bransden and Joachain, 2000] Bransden, B. H. and Joachain, C. J. (2000). Quantum mechanics 2nd edn, pages 447-457.
[Farhi et al., 2000] Farhi, E., Goldstone, J., Gutmann, S., and Sipser, M. (2000). Quantum computation by adiabatic evolution. *arXiv preprint quant-ph/*0001106.
[Garey et al., 1974] Garey, M. R., Johnson, D. S., and Stockmeyer, L. (1974). Some simplified np-complete problems. In *Proceedings of the sixth annual ACM symposium on Theory of computing*, pages 47-63. ACM.
[Hamerly et al., 2018] Hamerly, R., Inagaki, T., McMahon, P. L., Venturelli, D., Marandi, A., Onodera, T., Ng, E., Langrock, C., Inaba, K., Honjo, T., et al. (2018). Scaling advantages of all-to-all connectivity in physical annealers: the coherent ising machine vs. d-wave 2000q. *arXiv preprint arXiv:* 1805.05217.

[Helmberg and Rendl, 2000] Helmberg, C. and Rendl, F. (2000). A spectral bundle method for semidefinite programming. *SIAM Journal on Optimization*, 10(3):673-696.

[Inagaki et al., 2016] Inagaki, T., Haribara, Y., Igarashi, K., Sonobe, T., Tamate, S., Honjo, T., Marandi, A., McMahon, P. L., Umeki, T., Enbutsu, K., et al. (2016). A coherent ising machine for 2000-node optimization problems. *Science*, 354(6312):603-606.

[Johnson et al., 2011] Johnson, M. W., Amin, M. H., Gildert, S., Lanting, T., Hamze, F., Dickson, N., Harris, R., Berkley, A. J., Johansson, J., Bunyk, P., et al. (2011). Quantum annealing with manufactured spins. *Nature*, 473(7346):194.

[Kauffman et al., 2014] Kauffman, S., Niiranen, S., and Vattay, G. (2014). Uses of systems with degrees of freedom poised between fully quantum and fully classical states. U.S. Pat. No. 8,849,580.

[Kirkpatrick et al., 1983] Kirkpatrick, S., Gelatt, C. D., and Vecchi, M. P. (1983). Optimization by simulated annealing. *science*, 220(4598):671-680.

[McLachlan, 1964] McLachlan, A. (1964). A variational solution of the time-dependent schrodinger equation. *Molecular Physics*, 8(1):39-44.

[McMahon et al., 2016] McMahon, P. L., Marandi, A., Haribara, Y., Hamerly, R., Langrock, C., Tamate, S., Inagaki, T., Takesue, H., Utsunomiya, S., Aihara, K., et al. (2016). A fully programmable 100-spin coherent ising machine with all-to-all connections. *Science*, 354(6312):614-617.

[Nielsen and Chuang, 2010] Nielsen, M. A. and Chuang, I. L. (2010). *Quantum Computation and Quantum Information*. Cambridge University Press.

[Slater, 1930] Slater, J. C. (1930). Note on hartree's method. *Physical Review*, 35(2):210. [Unruh, 1995] Unruh, W. G. (1995). Maintaining coherence in quantum computers. *Physical Review A*, 51(2):992.

[Diaz, et al., 2011] Diaz, S., Venegas-Andraca, S., and Gomez-Munoz, Jose Luis (2011). Classical Simulation of Quantum Adiabatic Algorithms using Mathematics on GPUs. *International Journal of Unconventional Computing*, March 2011.

Unless otherwise indicated, all references disclosed herein are incorporated herein by reference in their entirety.

What is claimed is:

1. A hybrid quantum-classical computer, comprising:
   a first quantum processor comprising a first plurality of entangled qubits;
   a second quantum processor comprising a second plurality of entangled qubits;
   a first plurality of detectors coupled to the first quantum processor and configured to read a state of each of the first plurality of qubits;
   a classical processor coupled to the first plurality of detectors and configured to determine a first plurality of outputs based on the states of the first plurality of qubits, wherein the classical processor is configured to determine the first plurality of outputs using a weighted linear combination of the states of the first plurality of qubits, wherein the weights are based on interaction values between the qubits in first plurality of qubits and the qubits in the second plurality of qubits in a final Hamiltonian whose eigenvalue solution is desired; and
   a first plurality of signal generators coupled to the classical processor and the second quantum processor and configured to generate and apply a plurality of signals based on the first plurality of outputs to the second plurality of qubits.

2. The computer of claim 1, wherein the qubits are superconducting qubits.

3. The computer of claim 2, wherein the state comprises a charge quanta.

4. The computer of claim 2, wherein the state comprises a magnetic flux quanta.

5. The computer of claim 4, wherein the first plurality of detectors comprise a dc SQUID for each of the first plurality of qubits.

6. The computer of claim 4, wherein the first plurality of signal generators are configured to generate magnetic fields that are inductively coupled to the second plurality of qubits.

7. The computer of claim 6, wherein the first plurality of signal generators comprise a dc SQUID for each of the second plurality of qubits.

8. The computer of claim 1, wherein the qubits are optical qubits.

9. The computer of claim 8, wherein the state comprises a degenerate optical parametric oscillator phase.

10. The computer of claim 9, wherein the first plurality of detectors comprise homodyne detectors.

11. The computer of claim 8, wherein the first and second quantum processors comprise a field-programmable gate array (FPGA) configured to generate a feedback signal.

12. The computer of claim 11, wherein the first plurality of signal generators include the FPGA and are configured to combine the feedback signal with the first plurality of signals determined from the state of each of the first plurality of qubits.

13. The computer of claim 1, comprising:
    a second plurality of detectors coupled to the second quantum processor and the classical processor and configured to read a state of each of the second plurality of qubits, wherein the classical processor is further configured to determine a second plurality of outputs based on the states of the second plurality of qubits; and
    a second plurality of signal generators coupled to the classical processor and the first quantum processor and configured to generate and apply a second plurality of signals based on the second plurality of outputs to the first plurality of qubits.

14. The computer of claim 13, wherein the first plurality of detectors are configured to also operate as the second plurality of signal generators and the first plurality of signal generators are configured to also operate as the second plurality of detectors.

* * * * *